United States Patent [19]

Frei et al.

[11] Patent Number: 4,897,416
[45] Date of Patent: Jan. 30, 1990

[54] INSECTICIDES AND PARASITICIDES

[75] Inventors: Bruno Frei, Liestal; Anthony C. O'Sullivan, Basel, both of Switzerland

[73] Assignee: Ciba-Geigy Corporation, Ardsley, N.Y.

[21] Appl. No.: 153,696

[22] Filed: Feb. 8, 1988

[30] Foreign Application Priority Data

Feb. 18, 1987 [CH] Switzerland .................. 600/87-1

[51] Int. Cl.[4] ............... A61K 31/365; C07D 315/00
[52] U.S. Cl. .................................... 514/450; 549/264
[58] Field of Search .................. 549/264; 514/450; 536/7.1

[56] References Cited

U.S. PATENT DOCUMENTS

| | | | |
|---|---|---|---|
| 4,093,629 | 6/1978 | Fisher | 260/326.34 |
| 4,134,973 | 1/1979 | Fisher et al. | 424/180 |
| 4,156,720 | 5/1979 | Fisher et al. | 424/180 |
| 4,173,571 | 11/1979 | Chabala et al. | 260/343.41 |
| 4,199,569 | 4/1980 | Chabala et al. | 424/180 |
| 4,200,581 | 4/1980 | Fisher et al. | 424/180 |
| 4,201,861 | 5/1980 | Mrozik et al. | 536/17 A |
| 4,203,976 | 5/1980 | Fisher et al. | 424/180 |
| 4,206,205 | 6/1980 | Mrozik et al. | 424/180 |
| 4,328,335 | 5/1982 | Mrozik | 536/7.1 |
| 4,457,920 | 7/1984 | Mrozik | 424/180 |
| 4,469,682 | 9/1984 | Mrozik | 424/180 |
| 4,696,945 | 9/1987 | Frei et al. | 549/264 |

FOREIGN PATENT DOCUMENTS

| | | |
|---|---|---|
| 0110667 | 6/1984 | European Pat. Off. . |
| 0147852 | 7/1985 | European Pat. Off. . |
| 0154204 | 9/1985 | European Pat. Off. . |
| 0180539 | 5/1986 | European Pat. Off. . |
| 0184173 | 6/1986 | European Pat. Off. . |
| 0186043 | 7/1986 | European Pat. Off. . |
| 0203832 | 12/1986 | European Pat. Off. . |
| 3532794 | 4/1986 | Fed. Rep. of Germany . |
| WO/8602097 | 4/1986 | PCT Int'l Appl. . |
| 2166436 | 5/1986 | United Kingdom . |

OTHER PUBLICATIONS

A. Burger, "Medicinal Chemistry," Part I, 3rd ed., J. Wiley & Sons, (1970), p. 75.
H. Rennenberg, Phytochemistry, 21(12), 2771–2781, (1982).
Chem. Abstract, vol. 104, Mar. 31, 1986, 101735q, Wildsmith, J. A. W.

*Primary Examiner*—Richard L. Raymond
*Assistant Examiner*—M. W. Russell
*Attorney, Agent, or Firm*—Edward McC. Roberts

[57] ABSTRACT

The present invention relates to novel 5-oximino-13β-carbonylthiomilbemycin derivatives of formula I, to their preparation and to the use thereof for controlling pests. The invention further relates to pesticidal compositions which contain at least one of these compounds as active ingredient. The novel compounds have the general formula I

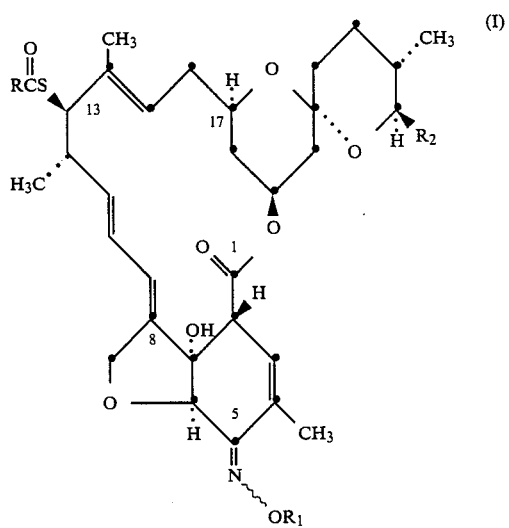

wherein
R$_1$ is hydrogen or an alkyl, cycloalkyl or acyl group,
R$_2$ is methyl, ethyl, isopropyl or sec-butyl, or is the

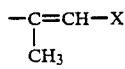

group, wherein X is methyl, ehtyl or isopropyl, and R is hydrogen or an unsubstituted or substituted straight chain or branched C$_1$–C$_{18}$alkyl group, an unsubstituted or substituted cycloaliphatic group of 3 to 10 carbon atoms, an unsubstituted or substituted C$_2$–C$_6$alkenyl group, an unsubstituted or substituted C$_2$–C$_6$alkynyl group, an unsubstituted or substituted phenyl group or an unsubstituted or substituted benzyl group.

14 Claims, No Drawings

INSECTICIDES AND PARASITICIDES

The present invention relates to novel 5-oximino-13β-carbonylthiomilbemycin derivatives of formula I, to their preparation and to the use thereof for controlling pests. The invention further relates to pesticidal compositions which contain at least one of these compounds as active ingredient.

The novel compounds have the general formula I

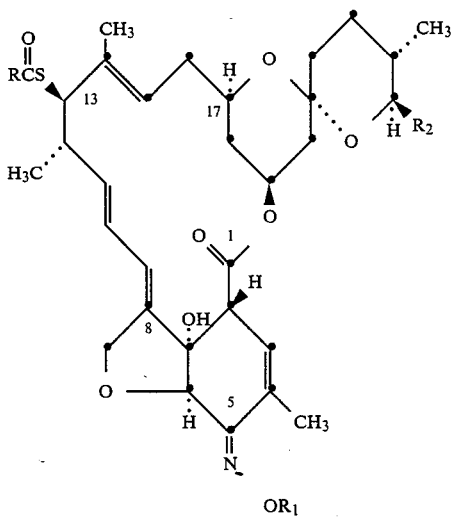

wherein $R_1$ is hydrogen or an alkyl, cycloalkyl or acyl group, $R_2$ is methyl, ethyl, isopropyl or sec-butyl, or is the

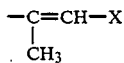

group, wherein X is methyl, ethyl or isopropyl, and R is hydrogen or an unsubstituted or substituted straight chain or branched $C_1-C_{18}$alkyl group, an unsubstituted or substituted cycloaliphatic group of 3 to 10 carbon atoms, an unsubstituted or substituted $C_2-C_6$alkenyl group, an unsubstituted or substituted $C_2-C_6$alkynyl group, an unsubstituted or substituted phenyl group or an unsubstituted or substituted benzyl group.

Particularly preferred compounds within the scope of this invention are the novel compounds of the general formula Ia

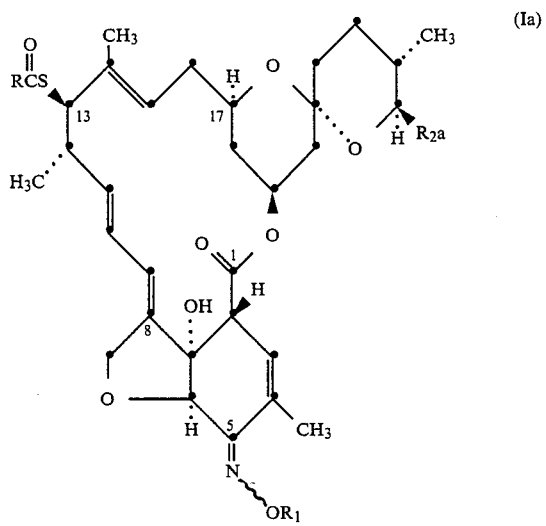

wherein $R_1$ is hydrogen or an alkyl, cycloalkyl or acyl group, $R_{2a}$ is methyl, ethyl, isopropyl or sec-butyl, and R is hydrogen, an unsubstituted or substituted straight chain or branched $C_1-C_{18}$alkyl group, an unsubstituted or substituted cycloaliphatic group of 3 to 10 carbon atoms, an unsubstituted or substituted $C_2-C_6$alkenyl group, an unsubstituted or substituted $C_2-C_6$alkynyl group, an unsubstituted or substituted phenyl group or an unsubstituted or substituted benzyl group.

Preferred meanings of the definitions cited above are: unsubstituted or halogenated $C_1-C_8$alkyl, unsubstituted $C_3-C_6$cycloalkyl or $C_3-C_6$cycloalkyl which is substituted by one or more methyl groups, adamantyl, unsubstituted or halogenated $C_2-C_6$alkenyl or $C_2-C_6$alkynyl, unsubstituted or substituted phenyl groups or unsubstituted or substituted benzyl groups.

Possible substituents of the alkyl, cycloalkyl, alkenyl and alkynyl groups are e.g. 1 to 7 halogen atoms or 1 to 6 $C_1-C_6$alkylthio and $C_1-C_6$alkoxy groups. Suitable substituents of the phenyl and benzyl groups are 1 to 3 members selected from the group consisting of halogen atoms, $C_1-C_6$alkyl, $C_1-C_6$alkoxy, $C_1-C_4$alkylthio, haloalkyl and nitro. The phenyl ring may also be substituted by a difluoromethylenedioxy group, in which case both oxygen atoms are located at directly adjacent carbon atoms of the phenyl ring. A suitable substituent of the alkyl group which is linked directly to the carboxylic acid radical is also an unsubstituted or substituted phenyl or phenoxy group, for example a halogenated phenyl or phenoxy group, preferably a phenyl or phenoxy group which is substituted by 1 to 3 halogen atoms. The cycloalkyl groups may also carry $C_1-C_4$alkyl groups as substituents, and a cyclopropyl group may also be substituted by a 2,2-dichlorovinyl group.

Depending on the stated number of carbon atoms, alkyl as by itself or as moiety of a substituent will be understood as meaning for example the following groups: methyl, ethyl, propyl, butyl, pentyl, hexyl, heptyl, octyl, nonyl or decyl, as well as the isomers thereof, e.g. isopropyl, isobutyl, tert-butyl or isopentyl. Haloalkyl is a mono- to perhalogenated alkyl substituent, e.g. $CHCl_2$, $CHF_2$, $CH_2Cl$, $CCl_3$, $CF_3$, $CH_2F$, $CH_2CH_2Cl$ or $CHBr_2$. Throughout this specification, halogen will be understood as meaning fluorine, chlorine, bromine or iodine, with fluorine, chlorine or bromine being preferred. Suitable cycloalkyl groups are mono- to tetracyclic groups, e.g. cyclopropyl, cyclobutyl, cyclopentyl, cyclohexyl, decalin, hydrindane, bicycloheptane, bicyclooctane, norbornane, bornane or adamantyl. These cycloaliphatic groups are preferably unsubstituted or substituted by one or more methyl groups. Alkenyl is an aliphatic, acyclic hydrocarbon radical characterised by at least one C=C double bond, and is e.g. vinyl, 1-propenyl, allyl, 1-butenyl, 2-butenyl or 3-butenyl. Haloalkenyl is therefore such an alkenyl radical which is substituted by one or more halogen atoms. Alkynyl is a straight chain or branched carbon chain which is characterised by at least one C≡C triple bond. Typical representatives are: ethynyl, 1-propynyl, propargyl or 1-butynyl. Alkoxyalkyl is an unbranched or branched alkyl group which is interrupted by an oxygen atom, e.g. $CH_2OCH_3$, $CH_2CH_2OCH_3$, $CH_2CH(CH_3)OCH_3$, $CH_2OC_2H_5$, $C(CH_3)_2OCH_3$, $iCH_2OC_3H_7$ or $CH_2CH_2CH_2OCH_3$.

Substituted phenyl is for example 2,6-dimethylphenyl, 2,4-dichlorophenyl, 2,3,6-trichlorophenyl, p-bromophenyl, 2,4-xylyl, 3-nitrophenyl, 4-chloro-2-methylphenyl, 4-methyl-2-methoxyphenyl, 2,4,6-trimethylphenyl or p-methylthiophenyl.

Without implying any limitation, R may be typically: hydrogen, methyl, ethyl, propyl, isopropyl, n-butyl, sec-butyl, tert-butyl, neopentyl, chloromethyl, trifluoromethyl, trichloromethyl, trichloroethyl, trichloro-tert-butyl, 1,2,2,2-tetrachloroethyl, 1,3,3,3-tetrachloropropyl, 3-chloropropyl, ethenyl, propenyl, methoxymethyl, isopropoxymethyl, 1-methyl-1-methoxyethyl, 2,2-dimethylvinyl, 1,2,2-trichlorovinyl, 1,3,3,3-tetrachloropropyl, 1,1-dichloro-2,2,2-trifluoroethyl, 1,3-pentadienyl, ethynyl, 1-propynyl, 1-butynyl, cyclopropyl, 2,2-dimethylcyclopropyl, 1-methylcyclopropyl, 2,2-dimethyl-3-(2,2-dichlorovinyl)-cyclopropyl, cyclobutyl, cyclopentyl, cyclohexyl, adamantyl, phenyl, benzyl, p-tolyl, p-chlorophenyl, 2,6-dichlorophenyl or 2,4-dinitrophenyl or 4-fluorophenoxymethyl, 2-trifluoromethylphenyl, 2,6-dimethylphenyl, 2-phenylethyl, 1-methyl-1-phenylethyl, 1-methoxy-1-methylethyl and 1-methyl-1-thiomethylethyl.

Compounds of formula I, wherein $R_1$ is hydrogen, are preferred. Examples of suitable acyl groups are the radicals $R_3$—C(O)—, wherein $R_3$ is $C_1$–$C_{10}$alkyl, $C_1$–$C_{10}$haloalkyl, or a phenyl or benzyl radical, each unsubstituted or substituted by substituents selected from the group consisting of halogen, $C_1$–$C_3$alkyl, $C_1$–$C_3$haloalkyl, $C_1$–$C_3$alkoxy, $C_1$–$C_3$haloalkoxy, cyano and nitro, with the preferred meanings of $R_3$ being $C_1$–$C_6$alkyl, $C_1$–$C_6$haloalkyl, or phenyl which is unsubstituted or substituted by halogen, $C_1$–$C_3$alkyl, $CF_3$ or nitro.

Compounds wherein $R_2$ is sec-butyl shall likewise be regarded as belonging to the class of milbemycin derivatives, although according to conventional classification they are derived from avermectin derivatives. However, avermectin aglycons (carrying an OH group in the 13α-position) can be converted into milbemycin homologues in accordance with U.S. Pat. No. 4 173 571.

Naturally occurring milbemycins ($R_2$=$CH_3$, $C_2H_5$ or isoC$_3$H$_7$) have solely hydrogen in 13-position instead of the thioester group of the instant compounds of formula I, as the following formula XXX shows:

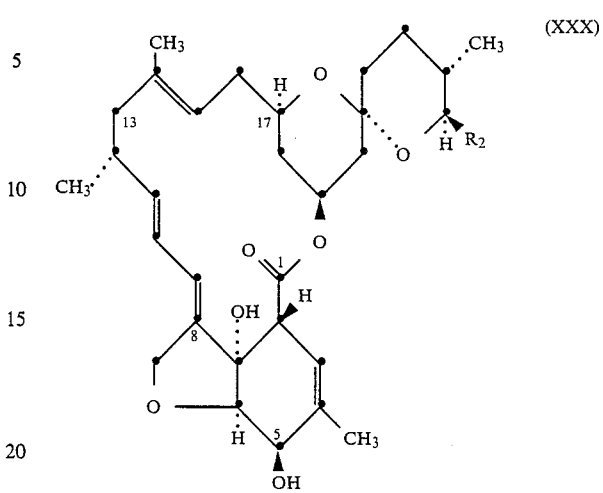

| | | (XXX) |
|---|---|---|
| $R_2$ = $CH_3$ | milbemycin $A_3$ | |
| $R_2$ = $C_2H_5$ | milbemycin $A_4$ | |
| $R_2$ = isoC$_3$H$_7$ | milbemycin D | |
| $R_2$ = sec-C$_4$H$_9$ | 13-deoxy-22,23-dihydro-C—076-Bla—aglycon. | |

Avermectins, however, carry in 13-position an α-L-oleandrosyl-α-L-oleandrose radical which is attached through oxygen in the α-configuration to the macrolide molecule. Moreover, avermectins differ structurally from milbemycins by the presence of a 23-OH group or $\Delta^{22,23}$ double bond and, usually, by the presence of a substituent $R_2$=sec-C$_4$H$_9$. Hydrolysis of the sugar residue of avermectins, readily affords the corresponding avermectinaglycons containing a 13α-hydroxy group which is adjacent to a C=C double bond. As stated above, avermectinaglycons can be converted into milbemycin homologues. In the milbemycin derivatives of the present invention, the $\Delta^{22,23}$ double bond is always in hydrogenated form and the substituent in the 13-position is always β-oriented.

Compounds of formula I, wherein $R_2$ is the

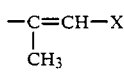

group and X is methyl, ethyl or isopropyl, represent those 23-deoxy derivatives of the naturally occurring antibiotics S541 which carry in 13-position a β-carbonylthio group and in 5-position an oximino group.

The constitution of naturally occurring antibiotics S541 is disclosed in DE 35 32 794 and is as follows:

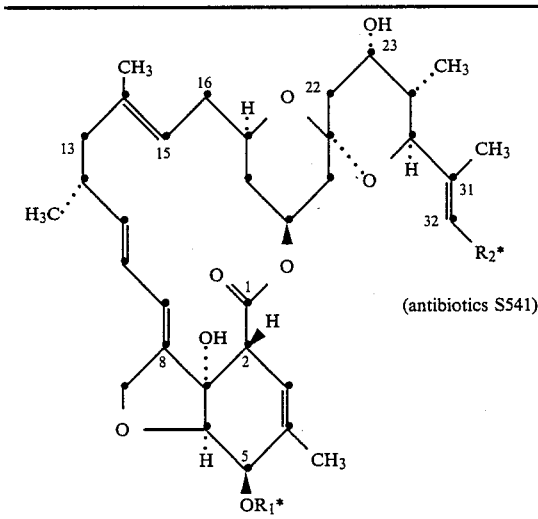

(antibiotics S541)

| | $R_2^*$ | $R_1^*$ |
|---|---|---|
| factor A | $R_2^* = isoC_3H_7$ | $R_1^* = H$ |
| factor B | $R_2^* = CH_3$ | $R_1^* = CH_3$ |
| factor C | $R_2^* = CH_3$ | $R_1^* = H$ |
| factor D | $R_2^* = C_2H_5$ | $R_1^* = H$ |
| factor E | $R_2^* = C_2H_5$ | $R_1^* = CH_3$ |
| factor F | $R_2^* = isoC_3H_7$ | $R_1^* = CH_3$ |

On account of their pronounced parasiticidal and insecticidal activity, the following subgroups of compounds of formula I are especially preferred:

Group Ia

Compounds of formula I, wherein $R_1$ is hydrogen, $R_2$ is methyl, ethyl, iropropyl or sec-butyl or is the

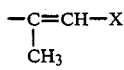

group, wherein X is methyl, ethyl or isopropyl, and R has the following meanings:

hydrogen; $C_1$-$C_6$alkyl, $C_2$-$C_4$alkenyl, $C_2$-$C_4$alkynyl or $C_3$-$C_6$cycloalkyl, each unsubstituted or substituted by 1 to 4 halogen atoms or 1 to 4 $C_1$-$C_4$alkylthio or $C_1$-$C_4$alkoxy groups;

phenyl or benzyl, each unsubstituted or substituted by 1 to 3 members selected from the group consisting of halogen, $C_1$-$C_4$alkyl, $C_1$-$C_4$alkylthio and nitro.

Group Ib

Compounds of formula I, wherein $R_1$ is hydrogen, $R_2$ is methyl, ethyl, isopropyl or sec-butyl or is the

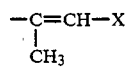

group, wherein X is methyl, ethyl or isopropyl and R has the following meanings:

hydrogen; $C_1$-$C_4$alkyl, $C_2$-$C_3$alkenyl, $C_2$-$C_3$alkynyl or $C_3$-$C_6$cycloalkyl, each unsubstituted or substituted by 1 to 4 chlorine or fluorine atoms or 1 to 4 methylthio or methoxy groups;

phenyl or benzyl, each unsubstituted or substituted by chlorine, fluorine, $C_1$-$C_2$alkyl, $C_1$-$C_2$alkoxy, $C_1$-$C_2$alkylthio or nitro.

Group Ic

Compounds of formula I, wherein $R_1$ is hydrogen, $R_2$ is methyl, ethyl, isopropyl or sec-butyl and R has the following meanings:

hydrogen: $C_1$-$C_6$alkyl, $C_2$-$C_4$alkenyl, $C_2$-$C_4$alkynyl or $C_3$-$C_6$cycloalkyl, each unsubstituted or substituted by 1 to 4 halogen atoms or 1 to 4 $C_1$-$C_4$alkylthio or $C_1$-$C_4$alkoxy groups;

phenyl or benzyl, each unsubstituted or substituted by 1 to 3 halogen atoms or 1 to 3 $C_1$-$C_4$alkyl, $C_1$-$C_4$alkoxy, $C_1$-$C_4$alkylthio or nitro groups.

Group Id

Compounds of formula I, wherein $R_1$ is hydrogen, $R_2$ is methyl, ethyl, isopropyl or sec-butyl, and R has the following meanings:

hydrogen; $C_1$-$C_4$alkyl, $C_2$-$C_3$alkenyl, $C_2$-$C_3$alkynyl or $C_3$-$C_6$cycloalkyl, each unsubstituted or substituted by 1 to 4 chlorine or fluorine atoms or 1 to 4 methylthio or methoxy groups;

phenyl or benzyl, each unsubstituted or substituted by chlorine, fluorine, $C_1$-$C_2$alkyl, $C_1$-$C_2$alkoxy, $C_1$-$C_2$alkylthio or nitro.

Group Ie

Compounds of formula I, wherein $R_1$ is hydrogen, $R_2$ is methyl or ethyl, and R has the following meanings:

hydrogen; $C_1$-$C_4$alkyl, $C_2$-$C_3$alkenyl, $C_2$-$C_3$alkynyl or $C_3$-$C_6$cycloalkyl, each unsubstituted or substituted by 1 to 4 chlorine or fluorine atoms or 1 to 4 methylthio or methoxy groups;

phenyl or benzyl, each unsubstituted or substituted by chlorine, fluorine, $C_1$-$C_2$alkyl, $C_1$-$C_2$alkoxy, $C_1$-$C_2$alkylthio or nitro.

Group If

Compounds of formula I, wherein $R_1$ is hydrogen, $R_2$ is isopropyl or sec-butyl, and R has the following meanings:

hydrogen; $C_1$-$C_4$alkyl, $C_2$-$C_3$alkenyl, $C_2$-$C_3$alkynyl or $C_3$-$C_6$cycloalkyl, each unsubstituted or substituted by 1 to 4 chlorine or fluorine atoms or 1 to 4 methylthio or methoxy groups;

phenyl or benzyl, each unsubstituted or substituted by chlorine, fluorine, $C_1$-$C_2$alkyl, $C_1$-$C_2$alkoxy, $C_1$-$C_2$alkylthio or nitro.

Group Ig

Compounds of formula I, wherein $R_1$ is hydrogen, $R_2$ is methyl, ethyl, isopropyl or sec-butyl or is the

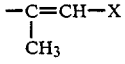

group, wherein X is methyl, ethyl or isopropyl, and R has the following meanings:

hydrogen; $C_1$-$C_4$alkyl, $C_2$-$C_3$alkenyl, $C_2$-$C_3$alkynyl or $C_3$-$C_6$cycloalkyl, each unsubstituted or substituted by 1 to 3 chlorine or fluorine atoms or 1 to 3 methylthio or methoxy groups;

phenyl or benzyl, each unsubstituted or substituted by chlorine, fluorine, $C_1$-$C_2$alkyl, $C_1$-$C_2$alkoxy, $C_1$-$C_2$alkylthio or nitro.

Group Ih

Compounds of formula I, wherein $R_1$ is hydrogen, $R_2$ is methyl, ethyl, isopropyl or sec-butyl, and R has the following meanings:

hydrogen; $C_1$-$C_4$alkyl, $C_2$-$C_3$alkenyl, $C_3$-$C_6$alkynyl or $C_3$-$C_6$cycloalkyl, each unsubstituted or substituted by 1 to 3 chlorine or fluorine atoms or 1 to 3 methylthio or methoxy groups;

phenyl or benzyl, each unsubstituted or substituted by chlorine, fluorine, $C_1$–$C_2$alkyl, $C_1$–$C_2$alkoxy, $C_1$–$C_2$alkylthio or nitro.

Group Ii

Compounds of formula I, wherein $R_1$ is hydrogen, $R_2$ is methyl or ethyl, and R has the following meanings:

hydrogen; $C_1$–$C_4$alkyl, $C_2$–$C_3$alkenyl, $C_2$–$C_3$alkynyl or $C_3$–$C_6$cycloalkyl, each unsubstituted or substituted by 1 to 3 chlorine or fluorine atoms or 1 to 3 methylthio or methoxy groups.

Group Ik

Compounds of formula I, wherein $R_1$ is hydrogen, $R_2$ is isopropyl or sec-butyl, and R has the following meanings:

hydrogen; $C_1$–$C_4$alkyl, $C_2$–$C_3$alkenyl, $C_2$–$C_3$alkynyl or $C_3$–$C_6$cycloalkyl, each unsubstituted or substituted by 1 to 3 chlorine or fluorine atoms or 1 to 3 methoxy groups.

Group Il

Compounds of formula I, wherein $R_1$ is hydrogen, $R_2$ is ethyl or methyl, and R has the following meanings: hydrogen, $C_1$–$C_8$alkyl which is unsubstituted or monosubstituted by $C_1$–$C_4$alkoxy, $C_1$–$C_4$alkylthio, phenyl or mono- to trihalogenated phenyl or phenoxy, or is substituted by 1 to 5 halogen atoms; a monocyclic to tetracyclic aliphatic group containing a total of 3 to 10 carbon atoms in the ring or ring system and which is unsubstituted or substituted by one or more members selected from the group consisting of $C_1$–$C_4$alkyl and halogenated $C_1$–$C_4$alkenyl; mono- to trihalogenated $C_2$–$C_4$alkenyl or $C_3$–$C_4$alkynyl; or phenyl or benzyl, each substituted by 1 to 3 substituents selected from the group consisting of halogen, $C_1$–$C_4$alkyl and nitro.

Group Im

Compounds of formula I, wherein $R_1$ is hydrogen, $R_2$ is ethyl or methyl, and R has the following meanings: hydrogen, $C_1$–$C_8$alkyl which is unsubstituted or substituted by 1 to 3 substituents selected from the group consisting of chlorine and fluorine; fluorophenoxymethyl, $C_3$–$C_4$cycloalkyl which is unsubstituted or substituted by a methyl group; adamantyl, trichlorovinyl, phenyl or monochlorophenyl.

Examples of especially preferred 5-oximino derivatives of formula I, wherein $R_1$ is hydrogen, are:

13$\beta$-formylthio-5-oximino-milbemycin D,
13$\beta$-acetylthio-5-oximino-milbemycin D,
13$\beta$-pivaloylthio-5-oximino-milbemycin D,
13$\beta$-formylthio-5-oximino-milbemycin $A_3$,
13$\beta$-acetylthio-5-oximino-milbemycin $A_3$,
13$\beta$-pivaloylthio-5-oximino-milbemycin $A_3$,
13$\beta$-formylthio-5-oximino-milbemycin $A_4$,
13$\beta$-acetylthio-5-oximino-milbemycin $A_4$,
13$\beta$-pivaloylthio-5-oximino-milbemycin $A_4$,
13$\beta$-(2'-methoxy-2'-methylpropionylthio)-5-oximino-milbemycin D,
13$\beta$-(2'-methoxy-2'-methylpropionylthio)-5-oximino-milbemycin $A_4$,
13$\beta$-trichloroacetylthio-5-oximino-milbemycin $A_4$,
13$\beta$-(4'-chloro-butanoylthio)-5-oximino-milbemycin $A_4$,
13$\beta$-trichloroacryloylthio-5-oximino-milbemycin $A_4$,
13$\beta$-cyclopropanecarbonylthio-5-oximino-milbemycin $A_4$,
13$\beta$-cyclobutanecarbonylthio-5-oximino-milbemycin $A_4$,
13$\beta$-heptanoylthio-5-oximino-milbemycin $A_4$,
13$\beta$-(3'-chloro-2',2'-dimethylpropionylthio)-5-oximino-milbemycin $A_4$,
13$\beta$-(3'-chloro-2',2'-dimethylpropionylthio)-5-oximino-milbemycin $A_3$,
13$\beta$-(1'-methyl-cyclopropanecarbonylthio)-5-oximino-milbemycin $A_4$,
13$\beta$-(1'-methyl-cyclopropanecarbonylthio)-5-oximino-milbemycin $A_3$,
13$\beta$-(1-adamantanecarbonylthio)-5-oximino-milbemycin $A_4$,
13$\beta$-(p-fluorophenoxyacetylthio)-5-oximino-milbemycin $A_4$,
13$\beta$-(2'-chloro-2'-methylpropionylthio)-4-oximino-milbemycin $A_4$,
13$\beta$-(2',2'-dichloropropionylthio)-5-oximino-milbemycin $A_4$,
13$\beta$-(2',2'-dimethylbutanoylthio)-5-oximino-milbemycin $A_4$,
13$\beta$-(3',3'-dimethylbutanoylthio)-5-oximino-milbemycin $A_4$,
13$\beta$-(2',2',3',3'-tetramethylbutanoylthio)-5-oximino-milbemycin $A_4$,
13$\beta$-(p-chlorobenzoylthio)-5-oximino-milbemycin $A_4$,
13$\beta$-(3',3',3'-trifluoropropionylthio)-5-oximino-milbemycin $A_4$,
13$\beta$-chloroacetylthio-5-oximino-milbemycin $A_4$
13$\beta$-(2'-chloro-3',3',3'-trifluorpropionylthio)-5-oximino-milbemycin $A_4$
13$\beta$-(3',3',3'-trifluoropropionylthio)-5-oximino-milbemycin $A_4$
13$\beta$-(4'-heptylcarbonylthio)-5-oximino-milbemycin $A_4$
13$\beta$-(4'-heptylcarbonylthio)-5-oximino-milbemycin $A_3$
13$\beta$-(2'-trifluoromethylbenzoylthio)-5-oximino-milbemycin $A_4$
13$\beta$-(2'-trifluoromethylbenzoylthio)-5-oximino-milbemycin $A_3$
13$\beta$-((R/S)-2'-phenylpropionylthio)-5-oximino-milbemycin $A_4$
13$\beta$-(R/S)-2'-phenylpropionylthio)-5-oximino-milbemycin $A_3$
13$\beta$-(2,2'-dimethylbutyrylthio)-5-oximino-milbemycin $A_4$
13$\beta$-(2,2'-dimethylbutyrylthio)-5-oximino-milbemycin $A_3$
13$\beta$-(3'-fluoro-2',2'-dimethylpropionylthio)-5-oximino-milbemycin $A_4$
13$\beta$-(3'-fluoro-2',2'-dimethylpropionylthio)-5-oximino-milbemycin $A_3$
13$\beta$-(methoxyacetylthio)-5-oximino-milbemycin $A_4$
13$\beta$-(methoxyacetylthio)-5-oximino-milbemycin $A_3$
13$\beta$-(2'3'-difluoromethylendioxy)benzoylthio-5-oximino-milbemycin $A_4$
13$\beta$-(2'3'-difluoromethylendioxy)benzoylthio-5-oximino-milbemycin $A_3$.

Particularly interesting compounds are those of formula I, wherein R is tert-butyl or 2-phenylpropyl and $R_1$ and $R_2$ are as defined for formula I. Among these compounds, those compounds are preferred in which $R_1$ is hydrogen and $R_2$ is methyl, ethyl or isopropyl.

Most preferred are compounds of formula Ia, wherein R is tert-butyl or 2-phenylpropyl, and $R_1$ and $R_{2a}$ are as defined for formula Ia. Among these compounds, those compounds are particularly preferred in which $R_1$ is hydrogen and $R_{2a}$ is methyl, ethyl or isopropyl.

The present invention relates not only to the compounds of formula I, but also to a process for their preparation. It has been found, namely, that the compounds of formula I are obtained by reacting a compound of formula II

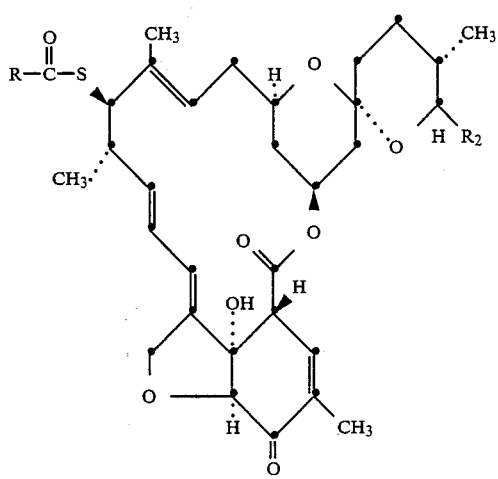

wherein R and $R_2$ are as defined for formula I, with a suitable oximating reagent.

Suitable oximating reagents are hydroxylamine ($NH_2OH$), hydroxylamine derivatives $NH_2OR_1$, wherein $R_1$ has the above defined meaning, or salts derived therefrom with mineral acids such as HCl, $NHO_3$ or $H_2SO_4$.

The reaction is normally carried out in an inert solvent such as methanol, ethanol, tetrahydrofuran, dioxan, pyridine, acetic acid, water or in a mixture of said solvents, in the temperature range from 0° to 80° C., preferably from 20° to 40° C.

If hydroxylamine is used in the form of a salt, e.g. as hydrochloride, then to neutralise the acid (e.g. HCl) it is convenient to add a base conventionally employed for this purpose and then to carry out the reaction in the presence of a hydrophilic agent, e.g. a molecular sieve. Suitable bases are organic and inorganic bases, e.g. tertiary amines such as trialkylamines (trimethylamine, trimethylamine, tripropylamine etc.), pyridine and pyridine bases (4-dimethylaminopyridine, 4-prrolidylaminopyridine etc.), oxides, hydrides and hydroxides, carbonates and bicarbonates of alkali metals and alkaline earth metals (CaO, BaO, NaOH, KOH, NaH, $Ca(OH)_2$, $KHCO_3$, $NaHCO_3$, $Ca(HCO_3)_2$, $K_2CO_3$, $Na_2CO_3$), as well as alkali metal acetates such as $CH_3COONa$ or $CH_3COOK$. Suitable bases are also alkali mtal alcoholates such as $C_2H_5ONa$, $n-C_3H_7ONa$ etc. Triethylamine is preferred.

Further, the compounds of formula I, wherein $R_1$ is an acyl group, can be obtained by reacting the compound of formula I, wherein $R_1$ is hydrogen, with an acid halide of formula III

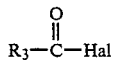

wherein $R_3$ has the given meaning and Hal is halogen, preferably chlorine or bromine.

The process is normally carried out in an inert solvent or in one of the reactants, provided they are liquid. Examples of suitable solvents are diethyl ether, tetrahydrofuran, dioxan, methylene chloride, carbon tetrachloride or chloroform. The reaction is usually carried out in the temperature range from −20° to +100° C., preferably from 0° to 50° C. To neutralise the acids formed as by-products it is convenient to carry out the reaction in the presence of neutralising agent.

Suitable neutralising agents are organic bases, for example tertiary amines such as trialkylamines (trimethylamine, triethylamine, diisopropylmethylamine or tripropylamine), 1,5-diazabicyclo[4.3.0]non-5-ene, 1,4-diazabicyclo[2.2.2]octane, 1,8-diazabicyclo[5.4.0]undec-7-ene, pyridine and pyridine bases (4-dimethylaminopyridine or 4-pyrrolidylaminopyridine). Pyridine is preferred. The neutralising agent is normally employed in at least equimolar amount, based on the starting materials.

The compounds of formula II are obtained from the compounds of formula IV

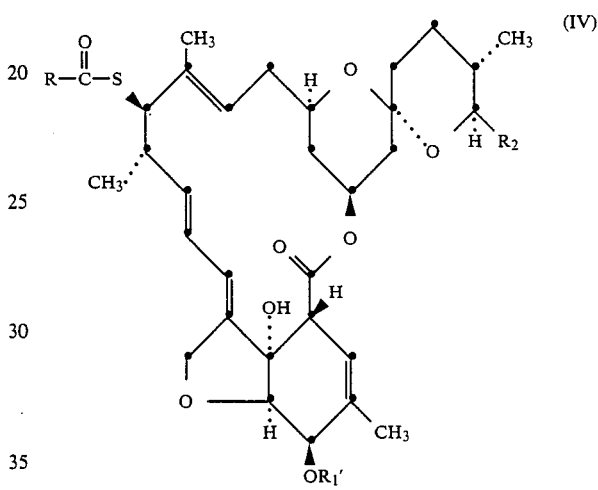

wherein $R_1'$ is hydrogen R and $R_2$ are as defined for formula I or II, by oxidation with a suitable reagent. Examples of suitable reagents are activated manganese dioxide, oxalyl chloride/dimethylsulfoxide/triethylamine, chromium trioxide/pyridine or further oxidising agents known to the skilled person. The reaction is normally carried out in an inert solvent.

Suitable solvents are hydrocarbons such as hexane, heptane, octane; aromatic hydrocarbons such as benzene, toluene, xylenes; and, preferably, chlorinated hydrocarbons, in particular methylene chloride. The reactions are carried out in the temperature range from −80° to +60° C., preferably from −60° to +30° C.

On account of their specific structure, the compounds of formula II are predestined for the preparation of the highly active compounds of formula I. They thus act as intermediates and some have also ecto- and endoparasitic properties like the final products. The compounds of formula II, including the processes for their preparation, likewise constitute an object of the present invention.

The present invention also relates to a process which makes possible the selective introduction of a β-acylthio group in the 13-position of milbemycin or 13-deoxy-22,23-dihydroavermectinaglycon derivatives or 23-deoxy-derivatives of the naturally occurring antibiotics S541 and hence to obtain the highly active novel parasiticides and insecticides of formula IV, which can also be used simultaneously for the preparation of further derivatives.

The thiol esters of formula IV, wherein RCOS— is in 13β-position, are prepared by starting from a compound of formula V

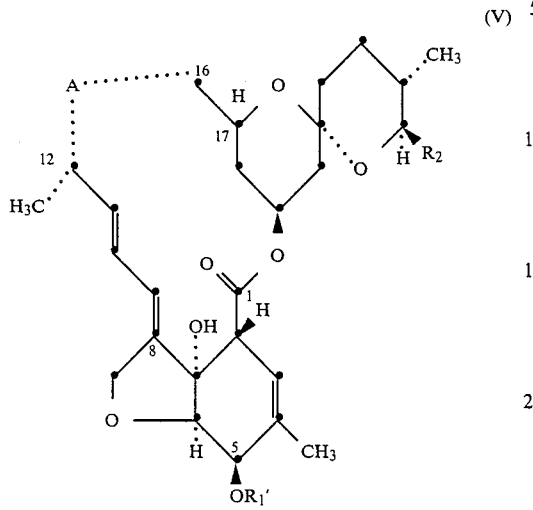

wherein A is a group a, b or c

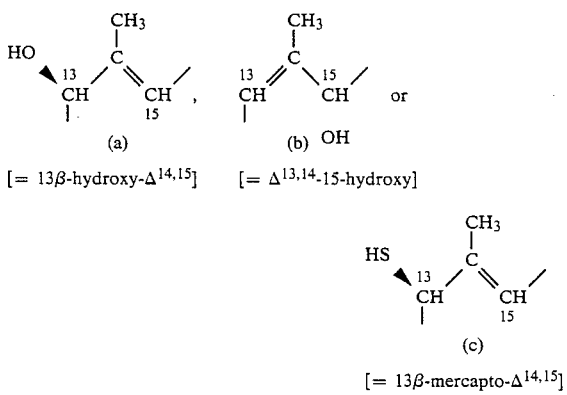

wherein $R_1'$ is hydrogen or a silyl or acyl group, and $R_2$ is as defined for formula I. A compound of formula V, wherein $R_1'$ is a protective group and $R_2$ is as defined for formula I, is treated with a reagent suitable for introducing or forming a 13β-thiol ester group. The $R_1'$ protective group, if it is desired to obtain a free 5-hydroxy compound, can thereafter be removed by hydrolysis.

Throughout this specification, OH protective groups $R_1'$ shall in general understood as being those protective functions customarily encountered in organic chemistry. Such protective groups are, in particular, acyl and silyl groups. Examples of suitable acyl groups are the radicals $R_4$—C(O)—, wherein $R_4$ is $C_1$-$C_{10}$alkyl, $C_1$-$C_6$haloalkyl, or a phenyl radical which is unsubstituted or substituted by halogen, $C_1$-$C_3$alkyl, $CF_3$ or nitro. Suitable silyl groups $R_1'$ are the radicals —Si($R_5$)($R_6$)($R_7$), wherein $R_5$, $R_6$ and $R_7$, preferably indpendently of one another, are $C_1$-$C_4$alkyl, benzyl or phenyl and form for example one of the groups trimethylsilyl, tris(tert-butyl)silyl, diphenyl-tert-butylsilyl, bis-(isopropyl)methylsilyl, dimethyl-(2,3-dimethyl-2-butyl)silyl, triphenylsilyl etc. or, preferably, tert-butyldimethylsilyl. The 5-OH group may also be in the form of benzyl ether or methoxyethoxymethyl ether.

Compounds of formula V, wherein A is the group a, are designated here and hereinafter as Va, the compounds containing group b as Vb, and the compounds containing group c as Vc.

Examples of reagents suitable for introducing the 13β-thiol ester group into compounds of formula Va and Vb are:

(a) thiocarboxylic acids of formula VI

RCOSH  (VI)

(b) thioamides of formula VII $RCSN(C_1-C_4alkyl)_2$  (VII)

wherein the alkyl moieties are preferably methyl.

Another process for the preparation of the thiol esters of formula I comprises reacting a compound of formula Vc with (c) an acid halide of formula VIII RCOhal  (VIII), wherein hal is halogen, preferably chlorine or bromine, or (d) an acid anhydride of formula IX $(RCO)_2O$  (IX)

In the above reactions the thiocarboxylic acids and thioamides are suitable for all compounds of formulae Va and Vb, but are preferably used for compounds of formula Vb, whereas acid halides and acid anhydrides are used for compounds of formula Vc.

In formulae VI to IX above, R is as defined for formula I.

The reactions to obtain compounds of formula IV are preferably carried out with compounds of formula Va or Vb, the reactive 5-hydroxy group of which is protected.

Compounds of formula IV, wherein $R_1'$ is a protective group, can be converted by simple, for example hydrolytic, removal of the protective function into the highly active free 5-hydroxy derivatives ($R_1'$=H) and thus act as intermediates. Moreover, the biological properties of these compounds are not diminished by the protective group.

The process for introducing the 13β-thiol ester group is normally carried out in an inert solvent or in one of the reactants, provided these are liquid. Examples of suitable solvents are: ether and ethereal compounds such as dialkyl ethers (diethyl ether, diisopropyl ether, tert-butylmethyl ether, dimethoxyethane, dioxan, tetrahydrofuran or anisole); halogenated hydrocarbons such as chlorobenzene, methylene chloride, ethylene chloride, chloroform, carbon tetrachloride or tetrachloroethylene; or sulfoxides such as dimethylsulfoxide; and also aromatic or aliphatic hydrocarbons such as benzene, toluene, xylene, petroleum ether, ligroin or cyclohexane. In some cases it can be advantageous to carry out the reactions in an inert gas atmosphere (e.g. argon, helium or nitrogen) and/or in absolute solvents. If desired, the final products can be purified in conventional manner, for example by washing, digestion, extraction, recrystallisation or chromatography. The reaction of compounds of formula Va or Vb with thiocarboxylic acids or thioamides of formula VI or VII takes place in the presence of orthoesters as well as in the presence of catalytic amounts of a further acid. Protic acids or Lewis acids may be used as acids which are suitable for this purpose. Examples of such acids are inorganic acids such as hydrohalic acids, e.g. hydrochloric acid, hydrobromic acid and hydriodic acid, perchloric acid and sulfuric acid, and organic acids such as acetic acid, trifluoroacetic acid, trichloroacetic acid, propionic acid, oxalic acid, formic acid, benzenesulfonic acid, p-toluenesulfonic acid or methanesulfonic acid, as well as Lewis acids such as $BF_3$, $AlCl_3$ or $ZnCl_2$. Especially preferred acids are p-toluenesulfonic acid (also referred to as TsOH) and sulfuric acid.

The orthoesters required for this reaction have the formula X $$R_8C(OR_9)_3 \qquad (X),$$

wherein $R_8$ is hydrogen or $C_1$-$C_4$alkyl, preferably methyl, and $R_9$ is $C_1$-$C_4$alkyl, preferably methyl or ethyl.

If thiocarboxylic acids or thioamides of formulae VI and VII respectively are used for the preparation of compounds of formula IV, the reaction temperatures are generally in the range from 0° to 150° C., preferably from 20° to 130° C.

The reaction of compounds of formula Vc with acid halides or acid anhydrides of formulae VIII and IX respectively is normally carried out in the inert solvents cited above and in the temperature range from −20° to +100° C., preferably from 0° to 70° C. To neutralise the acids formed as by-products, it is convenient to carry out the reaction in the presence of one of the neutralising agents cited above, preferably pyridine.

During the reaction of compounds of formula Vb with thiocarboxylic acids of formula VI or thioamides of formula VII in the presence of orthoesters of formula X and a catalytically effective acid, in addition to the compounds of formula I, compounds of formula XI

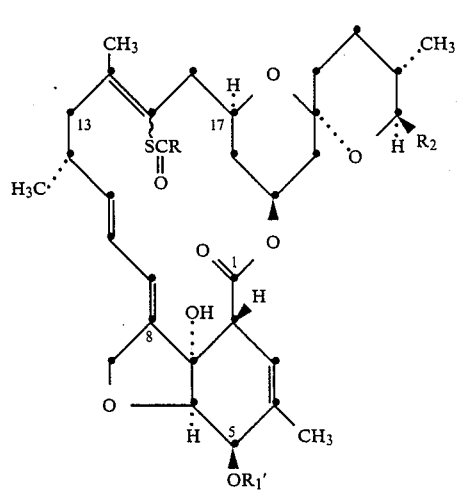

(XI)

wherein $R_1'$, $R_2$ and R are as defined for formula IV, may also be formed as by-products.

The reaction products so obtained can be separated by conventional separation methods, e.g. by fractional crystallisation or by chromatography. Chromatography will be understood as meaning column, thick-layer or thin-layer chromatography as well as, preferably, high-pressure liquid chromatography over mineral carriers such as silica gel or over organic exchange resins.

The compounds of formulae Va and Vb, wherein $R_2$ is methyl, ethyl, isopropyl or sec-butyl and $R_1'$ is hydrogen or a silyl or an acyl group, are disclosed in published European patent applications 180 539 and 147 852.

Compounds of formula Va and Vb, wherein $R_2$ is the

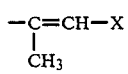

group and X is methyl, ethyl or isopropyl and $R_1'$ is hydrogen or a silyl or acyl group, can be prepared by methods analogous to known ones from the naturally occurring antibiotics S541 which are known from DE 35 32 794 and are characterised by the following chemical structure:

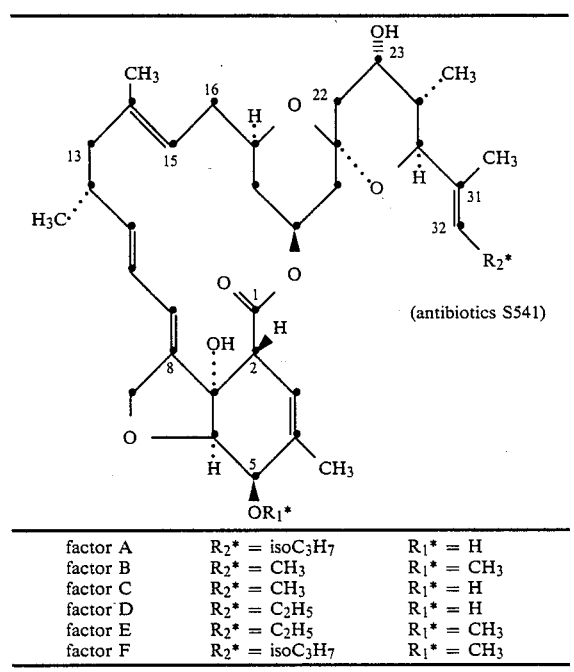

(antibiotics S541)

| | | |
|---|---|---|
| factor A | $R_2^* = isoC_3H_7$ | $R_1^* = H$ |
| factor B | $R_2^* = CH_3$ | $R_1^* = CH_3$ |
| factor C | $R_2^* = CH_3$ | $R_1^* = H$ |
| factor D | $R_2^* = C_2H_5$ | $R_1^* = H$ |
| factor E | $R_2^* = C_2H_5$ | $R_1^* = CH_3$ |
| factor F | $R_2^* = isoC_3H_7$ | $R_1^* = CH_3$ |

Depending on the factor, the derivatives of antibiotics S541 will be hereinafter classified as derivatives of S541A, S541B, S541C, S541D, S541E or S541F in order to simplify their designation.

The hydroxy group in 23-position in the antibiotics S541 can be removed by a method analogous to that described in U.S. patent specification 4 328 335, and the antibiotics S541 can thus be converted into the corresponding 23-deoxy derivatives. For this conversion it is necessary first to protect selectively those compounds having a free 5-hydroxy group ($R_1^*$=H) by reaction with one of the aforementioned silylating reagents Y—Si($R_5$)($R_6$)($R_7$) or with tert-butyldimethylsilyloxyacetyl chloride. The reaction of these protected compounds, in which $R_1^*$ is replaced by Si($R_5$)($R_6$)($R_7$) or C(=O)C-$H_2$OSi($CH_3$)$_2$t-$C_4H_9$ and the 23-C-atom is substituted by OH, with p-methylphenylchlorothionoformate gives derivatives of antibiotics S541 which are substituted in 23-position by p—$CH_3$—$C_6H_4$—O—C(=S)—O—. These 23-O-(4-methylphenoxy)thiocarbonyl derivatives of antibiotics S541 are then used as starting meterials for the reduction with tributyltin hydride, in toluene and in the presence of azobisisobutyronitrile at 80°–120° C., to give the corresponding 23-deoxy derivatives (position 23 unsubstituted).

The preparation of compounds of formula Vc can be effected by reacting a compound of formula Vb with a halothionoformate of formula XII

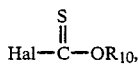
(XII)

wherein $R_{10}$ is $C_2$–$C_{10}$haloalkyl, and subsequently reducing the resultant product.

The reaction of compounds of formula Vb with halothionoformates of formula XII is normally carried out in the aforementioned (for the introduction of the 13β-thiol ester group) inert solents or in the halothionoformate of formula XII itself. The process is conveniently carried out in the presence of a condensing agent. Suitable condensing agents are organic and inorganic bases, e.g. tertiary amines such as trialkylamines (trimethylamine, triethylamine, tripropylamine etc.), pyridine and pyridine bases (4-dimethylaminopyridine, 4-pyrrolidylaminopyridine etc.). Pyridine is preferred. The condensing agent is normally employed in at least equimolar amount, based on the starting materials. The reaction temperatures for this reaction are generally in the range from −50° to +150° C., preferably from −20° to +100° C. The thiolcarbonates of formula IV (R=$OR_{10}$) formed during this reaction can be converted by simple reduction, e.g. with zinc in glacial acetic acid, into 13β-mercapto compounds of formula Vc. This reduction is conveniently carried out in a conventional inert organic solvent (for example one of those cited above), in the temperature range from 0° to 50° C., preferably from 20° to 50° C.

All those derivatives of formulae IV, Va, Vb, and Vc, wherein $R_i'$ has a meaning other than hydrogen ($R_1'$=OH protective group), are prepared by acylating or silylating the 5-OH group. The introduction of the acyl group is usually effected with the corresponding acyl halides or acyl anhydrides, preferably to introduce the $R_4C(O)$-group mentioned above. For the silylation it is convenient to use a silane of the formula Y—Si($R_5$)($R_6$)($R_7$), wherein each of $R_5$, $R_6$ and $R_7$ is one of the radicals indicated above. The term acyl halide denotes acyl chloride or acyl bromide and Y is a silyl leaving group. Examples of silyl leaving groups Y are bromide, chloride, cyanide, azide, acetamide, trifluoroacetate or trifluoromethanesulfonate. This recitation constitutes no limitation; further typical silyl leaving groups are known to the skilled person.

5-O-Acylations and 5-O-silylations are carried out in anhydrous medium, preferably in inert solvents and, most preferably, in aprotic solvents. The reaction conveniently takes place in the temperature range from 0° to 80° C., preferably from 10° to 40° C. It is preferred to add an organic base. Examples of suitable bases are tertiary amines such as triethylamine, triethylenediamine, triazole and, preferably, pyridine, imidazole or 1,8-diazabicyclo[5.4.0]-undec-7-ene (DBU).

The removal of these silyl and acyl radicals $R_1'$ in 5-position is effected by selective mild hydrolysis (→$R_1'$=H), for example with arylsulfonic acid in alcoholic solution or by another method known to the skilled person.

The described process for the preparation of compounds of formula I constitutes in all its partial steps an object of the present invention.

Particularly preferred within the scope of this invention is a process for the preparation of compounds of formula Ia The compounds of formula I are most suitable for controlling pests of animals and plants in all development stages, including in particular ectoparasites of animals. These last mentioned pests comprise those of the order Acarina, in particular pests of the families Ixodidae, Dermanyssidae, Sarcoptidae, Psoroptidae; of the orders Mallophaga, Siphonaptera, Anoplura (e.g. family of the Haematopinidae); and of the order Diptera, in particular pests of the families Muscidae, Calliphoridae, Oestridae, Tabanidae, Hippoboscidae, and Gastrophilidae.

The compounds of formula I can also be used to combat hygiene pests, especially those of the order Diptera (families Sarcophagidae, Anophilidae and Culicidae); of the order Orthoptera, of the order Dictyoptera (e.g. family of the Blattidae), and of the order Hymenoptera (e.g. family of the Formicidae).

The compounds of formula I also have a lasting action against mites and inserts which are parasites of plants. When used to control spider mites of the order Acarina, they are effective against eggs, nymphs and adults of Tetranychidae (tetranychus spp. and Panonychus spp.). They also have excellent activity against sucking insects of the order Homoptera, in particular against pests of the families Aphididae, Delphacidae, Cicadellidae, Psyllidae, Coccidae, Diaspididae and Eriophyidae (e.g. the rust mite on citrus fruit); of the orders Hemiptera, Heteroptera and Thysanoptera; and against plant-feeding insects of the orders Lepidoptera, Coleoptera, Diptera and Orthoptera.

The compounds of formula I are also suitable for use as soil insecticides for controlling pests in the soil.

The compounds of formula I are therefore effective against all development stages of sucking and feeding insects in crops such as cereals, cotton, rice, maize, soybeans, potatoes, vegetables, fruit, tobacco, hops, citrus fruit, avocados and others.

The compounds of formula I are also effective against plant nematodes of the genera Meloidogyne, Heterodera, Pratylenchus, Ditylenchus, Radopholus, Rhizoglyphus and others.

Further, compounds of formula I act against helminths in all development stages, among which the endoparasitic nematodes can be the cause of severe diseases in mammals and fowl, for example in sheep, pigs, goats, cattle, horses, donkeys, dogs, cats, guinea pigs, cage-birds. Typical nematodes having this indication are: Haemonchus, Trichostrongylus, Ostertagia, Nematodirus, Cooperia, Ascaris, Bunostomum, Oesphagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. The particular advantage of the compounds of formula I is their effectiveness against those parasites that are resistant to benzimidazole-based parasiticides.

Certain species of the genera Nematodirus, Cooperia and Oesophagostomum attack the intestinal tract of the host animal, whereas others of the genera Haemonchus and Ostertagia parasiticise in the stomach and those of the genus Dictyocaulus in the lung tissue. Parasites of the families Filariidae and Setariidae are found in internal cell tissue and internal organs, e.g. in the heart, blood vessels, lymph vessels and in subcutaneous tissue. In this connection, particular mention is to be made of the dog heartworm, Dirofilaria immitis. The compounds of formula I are highly effective against these parasites.

The compounds of formula I are also suitable for controlling pathogenic parasites in humans, among which parasites there may be mentioned as typical representatives occurring in the alimentary tract those of the genera Ancylostoma, Necator, Ascaris, Strongyloides, Trichinella, Capillaria, Trichuris and Enterobius. The compounds of this invention are also effective against parasites of the genera Wuchereria, Brugia, Onchocerca and Loa of the family of the Filariidae which occur in the blood, in tissue and various organs, and, in addition, against Dracunculus and parasites of the genera Strongyloides and Trichinella which infest in particular the gastro-intestinal tract.

The compounds of formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The compounds of formula I are administered to warm-blooded animals at rates of application of 0.01 to 10 mg/kg of body weight. They are applied to enclosed crop areas in amounts of 10 g to 1000 g per hectare. They are also used in pens, livestock buildings or other buildings.

The formulations, i.e. the compositions or mixtures containing the compound of formula I (active ingredient) are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixture or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the active ingredient to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$-$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$-$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide; or phospholipids.

The surfactants customarily employed in the art of formulation are described e.g. in "1986 International McCutcheon's Emulsifiers and Detergents", The Manufacturing Confectioner Publishing Co., Glen Rock, N.J., USA.

The pesticidal compositions usually contain 0.01 to 95%, preferably 0.1 to 80%, of a compound of formula I, 5 to 99.99% of a solid or liquid adjuvant, and 0 to 25%, preferably 0.1 to 25%, of a surfactant.

Whereas commercial products are preferably formulated as concentrates, the end user will normally employ dilute formulations having a concentration of 1-10 000 ppm.

The invention therefore also relates to pesticidal compositions which contain as active ingredient at least one compound of formula I, together with customary carriers and/or dispersing agents.

The compositions may also contain further ingredients, such as stabilisers, antifoams, viscosity regulators, binders, tackifiers as well as fertilizers or other active ingredients for obtaining special effects.

PREPARATORY EXAMPLES

1. Preparation of starting materials and intermediates

Example P1

Preparation of 13β-mercaptomilbemycin D and of 5-O-tert-butyldimethylsilyl-13β-mercaptomilbemycin D (a) With stirring and under argon, 0.1 ml (157 mg; 0.689 mmol) of 2,2,2-trichloroethylchlorothionoformate is added dropwise at −10° C. to a solution of 209 mg (0.305 mmol) of 5-O-tert-butyldimethylsilyl-15-hydroxy-$\Delta^{13,14}$-milbemycin D and 0.012 ml (120 mg; 1.52 mmol) of pyridine in 3 ml of dichloromethane. After stirring for 1 hour at room temperature, working up is effected with 5% aqueous NaHCO$_3$ solution and diethyl ether. Chromatography of the crude product [20 g of silica gel/eluant: 1:4 mixture of ethyl acetate/hexane] yields 282 mg of 5-O-tert-butyldimethylsilyl-13β-2,2,2-trichloroethoxycarbonylthiomilbemycin D which still contains some impurities.

A suspension of 320 mg (4.9 mmol) of zinc powder in a solution of 227 g of the above crude product in 0.5 ml of diethyl ether, 2 ml of 90% aqueous acetic acid and 3 drops of HCl (1M) is stirred for 16 hours at room temperature under argon. The mixture is diluted with diethyl ether, filtered through Celite, dried over MgSO$_4$ and concentrated. Chromatography of the crude product [20 g of silica gel/eluant: 12:88 mixture of ethyl acetate/hexane] yields 72 mg (40%) of 5-O-tert-butyldimethylsilyl-13β-mercaptomilbemycin D.

(b) This purified product is stirred for 2 hours at room temperature with 2 ml of a 1% solution of p-toluenesulfonic acid in methanol. After working up with 5% aqueous NaHCO$_3$ solution and diethyl ether, the crude product is chromatographed [20 g of silica gel/eluant: 2:3 mixture of ethyl acetate/hexane], affording 54 mg (89%) of 13β-mercaptomilbemycin D for which the following spectroscopic data are obtained:

$^1$H-NMR (300 MHz; CDCl$_3$; TMS),
1.61 ppm (s) (C$_{14}$CH$_3$),
1.87 ppm (s) (C$_4$CH$_3$),
3.31 ppm (dd; J=5.4 and 10.9), (C$_{13}$H),
mass spectrum m/e: 588 (M$^+$, C$_{33}$H$_{48}$O$_7$S) 460, 309, 277, 209, 181.

Example P2

Preparation of 5-O-tert-butyldimethylsilyl-13β-trichloroethoxycarbonylthiomilbemycin A$_4$ With stirring and under argon, 0.13 ml (205 mg; 0.9 mmol) of 2,2,2-trichloroethylchlorothionoformate are added dropwise at −10° C. to a solution of 100 mg (0.15 mmol) of 5-O-tert-butyldimethylsilyl-15-hydroxy-$\Delta^{13,14}$-milbemycin A$_4$ and 0.060 ml (59 mg; 0.75 mmol) of pyridine in 3 ml of dichloromethane. After stirring for 30 minutes at room temperature, working up is effected with 5% aqueous NaHCO$_3$ solution and diethyl ether. Chromatography of the crude product [20 g of silica gel/eluant: 1:12 mixture of ethyl acetate/hexane] yields 40 mg of 5-O-tert-butyldimethylsilyl-13β-2,2,2-trichloroethoxycarbonylthiomilbemycin A$_4$.

$^1$H-NMR (300 MHz; CDCl$_3$; TMS),
3.82 ppm (d, J=10 Hz) (C$_{13}$H),
4.75 ppm (d, J=14 Hz) and 4.86 (d) (J=14 Hz) (Cl$_3$CCH$_2$),
mass spectrum (FD) m/e: 862 (M$^+$, C$_{41}$H$_{61}$Cl$_3$O$_9$SSi).

Example P3

Preparation of 5-O-tert-butyldimethylsilyl-13β-mercaptomilbemycin A$_4$

A solution of 2.9 g (3.36 mmol) of 5-O-tert-butyldimethylsilyl-13β-2,2,2-trichloroethoxycarbonylthiomilbemycin A$_4$ in 40 ml of tetrahydrofuran is rapidly stirred for 5 hours with 1.05 g (16.1 mmol) of zinc and 20 ml of saturated aqueous NH$_4$Cl. Working up is effected with water and diethyl ether. Chromatography of the crude product [silica gel/eluant: 1:9 mixture of ethyl acetate/hexane] yields 2.46 g of 5-O-tert-butyldimethylsilyl-13β-mercaptomilbemycin A$_4$.

$^1$H-NMR (300 MHz; CDCl$_3$; TMS),
3.29 ppm (dd; J=10 and 5 Hz) (C$_{13}$H),
mass spectrum (FD) m/e: 688 (M$^+$, C$_{38}$H$_{60}$O$_7$SSi).

Example P4

Preparation of 5-O-tert-butyldimethylsilyl-13β-(4'-heptylcarbonylthio)milbemycin A$_4$ and of 13β-(4'-heptylcarbonylthio)milbemycin A$_4$ (a) With stirring and under argon, 0.2 ml of 4-heptylcarbonyl chloride are added at 0° C. to a solution of 110 mg (0.154 mmol) of 5-O-tert-butyldimethylsilyl-13β-mercaptomilbemycin A$_4$ in 5 ml of absolute chloroform and 2 ml of pyridine. After stirring for 7 hours at room temperature, working up is effected with ice-cold dilute aqueous HCl, dilute aqueous NaHCO$_3$ solution and diethyl ether. Chromatography of the crude product [10 g of silica gel/eluant: 1:5 mixture of ethyl acetate/hexane] yields 92 mg of 5-O-tert-butyldimethylsilyl-13β-(4'-heptylcarbonylthio)milbemycin A$_4$.

(b) This purified product is stirred for 3 hours at room temperature with 1 ml of a 1% solution of p-toluenesulfonic acid in methanol. After working up with 5% aqueous NaHCO$_3$ solution and diethyl ether, the crude product is chromatographed [10 g of silica gel/eluant: 1:3 mixture of ethyl acetate/hexane], affording 49 mg of 13β-(4'-heptylcarbonylthio)milbemycin A$_4$ for which the following spectroscopic data are obtained:

$^1$H-NMR (300 MHz; CDCl$_3$; TMS),
3.95 ppm (d, J=6 Hz) (C$_6$H),
3.97 ppm (d, J=10 Hz) (C$_{13}$H),
MS (FD) m/e: 700 (M$^+$, C$_{40}$H$_{60}$O$_8$S).

The following compounds are prepared in accordance with Example P4:

Example P5

13β-acetylthiomilbemycin A$_4$

MS (FD) m/e: 616 (M$^+$, C$_{34}$H$_{48}$O$_8$S).

Example P6

13β-(2'-trifluoromethylbenzoylthio)milbemycin A$_4$ $^1$H-NMR (300 MHz; CDCl$_3$; TMS),
3.97 ppm (d, J=6 Hz) (C$_6$H),
4.21 ppm (d, J=10 Hz) (C$_{13}$H),
7.48–7.76 ppm (m) (4 aromat. H),
MS (FD) m/e: 746 (M$^+$, C$_{40}$H$_{49}$O$_9$SF$_3$).

Example P7

13β-((R/S)-2'-phenylpropionylthio)milbemycin A₄; mixture of diastereoisomers

¹H-NMR (300 MHz; CDCl₃; TMS),
3.75 and 3.83 ppm (2 q, J=6 Hz) (C'₂, H),
3.82 and 3.93 ppm (2 d, J=6 Hz) (C₆H),
3.81 and 3.94 ppm (2 d, J=10 Hz) (C₁₃H),
7.11–7.37 ppm (m) (5 aromat. H).

Example P8

13β-(2', 2'-dimethylbutyrylthio)milbemycin A₄

¹H-NMR (300 MHz; CDCl₃; TMS),
3.91 ppm (d, J=10 Hz) (C₁₃H),
3.95 ppm (d, J=6 Hz) (C₆H),
MS (FD) m/e: 672 (M³⁰, C₃₈H₅₆O₈S).

Example P9

13β-(3'-chloro-2', 2'-dimethylpropionylthio)milbemycin A₄

¹H-NMR (300 MHz; CDCl₃; TMS),
3.93 ppm (d, J=10 Hz) (C₁₃H),
3.96 ppm (d, J=6 Hz) (C₆H),
3.60 ppm (AB-system, J=13 Hz; A-part; 3.57 ppm, B-part; 3.63 ppm) (CH₂Cl).

Example P10

13β-(2'-methyl-2'-phenylpropionylthio)milbemycin A₄

¹H-NMR (300 MHz; CDCl₃; TMS),
3.89 ppm (d, J=11 Hz) (C₁₃H),
3.96 ppm (d, J=6 Hz) (C₆H),
7.19–7.37 ppm (m) (5 aromat. H).

Example P11

13β-(3'-fluoro-2',2'-dimethylpropionylthio)milbemycin A₄

¹H-NMR (300 MHz; CDCl₃; TMS),
3.94 ppm (d, J=6 Hz) (C₆H),
3.98 ppm (d, J=10 Hz) (C₁₃H),
4.37 ppm (d, J=47 Hz) (CH₂F),
MS (FD) m/e: 676 (M+, C₃₇H₅₃FO₈S).

Example P12

13β-methoxyacetylthiomilbemycin A₄

¹H-NMR (300 MHz; CDCl₃; TMS),
3.94 ppm (d, J=6 Hz) (C₆H),
4.03 ppm (d, J=10 Hz) (C₁₃H),
3.45 ppm (s) (CH₃OCH₂),
4.04 ppm (s) (CH₃OCH₂),
MS (FD) m/e: 646 (M+, C₃₅H₅₀O₉S).

Example P13

13β-((S)-2'-phenylpropionylthio)milbemycin A₄

¹H-NMR (300 MHz; CDCl₃; TMS),
3.83 ppm (q, J=6 Hz) (C₂, H),
3.93 ppm (d, J=6 Hz) (C₆H),
3.94 ppm (d, J=10 Hz) (C₁₃H),
7.18–7.37 ppm (m) (5 aromat. H).

Example P14

13β-((R)-2'-phenylpropionylthio)milbemycin A₄

¹H-NMR (300 MHz; CDCl₃; TMS),
3.75 ppm (q, J=6 Hz) (C₂, H),
3.81 ppm (d, J=10 Hz) (C₁₃H),
3.82 ppm (d, J=6 Hz) (C₆H),
7.11–7.26 ppm (m) (5 aromat. H).

Example P15

Preparation of 13β-pivaloylthiomilbemycin A₄

A solution of 280 mg (0.416 mmol) of 5-O-tert-butyldimethylsilyl-15-hydroxy-Δ¹³,¹⁴-milbemycin A₄, 0.4 ml of trimethyl orthoacetate and 0.4 ml of thiopivalic acid in 4 ml of toluene is heated for 6 hours to 60° C. Working up is effected with diethyl ether and 5% aqueous NaHCO₃ solution. Chromatography through silica gel (eluant: 1:6 mixture of ethyl acetate/hexane) yields 61 mg of 5-O-tert-butyldimethylsilyl-13β-pivaloylthiomilbemycin A₄.

This product is treated for 2 hours at room temperatuare with 2 ml of a 40% aqueous solution of HF and acetonitrile (5:95). Working up in diethyl ether with 5% aqueous NaHCO₃ solution and chromatography over silica gel (eluant: 1:2 mixture of ethyl acetate/hexane) yield 21 mg of 13β-pivaloylthiomilbemycin A₄.

1H-NMR (250 MHz; CDCl₃; TMS),
1.25 ppm (s)[(CH₃)₃C],
3.97 ppm (d)(J=10 Hz)(C₁₃H),
4.01 ppm (d)(J=6 Hz)(C₆H).

Example P16

Preparation of 13β-acetylthiomilbemycin A₄
13β-Acetylthiomilbemycin A₄ is prepared in accordance with Example P15

¹H-NMR (300 MHz; CDCl₃; TMS),
2.32 ppm (s)(CH₃COS),
3.96 ppm (d, J=6 Hz)(C₆H),
4.03 ppm (d, J=10 Hz)(C₁₃H).

2. Preparation of final products of formula I

Example F1

Preparation of 13β-pivaloylthio-5-oximinomilbemycin A₄

(a) A solution of 49 mg (0.075 mmol) of 13β-pivaloylthiomilbemycin A₄ in 2 ml of dichloromethane is vigorously stirred for 30 minutes at room temperature with 98 mg of manganese dioxide. The manganese dioxide is removed by filtration through Celite and concentration of the solution yields crude 13β-pivaloylthio-5-ketomilbemycin.

(b) The above crude product and 8 mg (0.12 mmol) of hydroxylamine hydrochloride are dissolved in 1 ml of pyridine. After stirring for 30 minutes at room temperature, working up is effected with diethyl ether and 2M aqueous HCl. Chromatography of the curde produce [20 g of silica gel/eluant: 1:4 mixture of ethyl acetate/hexane] affords 15 mg (29%) of 13β-pivaloylthio-5-oximinomilbemycin A₄.

¹H-NMR (300 MHz; CDCl₃; TMS),
3.36 ppm (m) (C₂H),
3.93 ppm (d; J=10) (C₁₃H),
5.77 ppm (s) (C₃H),
mass spectrum (FD) m/e: 671 (M+, C₃₇H₅₄NO₈S).

Example F2

Preparation of 13β-(4'-heptylcarbonylthio)-5-oximinomilbemycin A₄

(a) 128 mg (1.47 mmol) of activated manganese dioxide are added to a solution of 30 mg (0.043 mmol) of 13β-(4'-heptylcarbonylthio)milbemycin A4 in 10 ml of abs. methylene chloride. The mixture is vigorously stirred for 20 minutes at room temperature, filtered through Hyflo and the filtrate is concentrated, affording 27 mg of 13β-(4'-heptylcarbonylthio)-5-oxomilbemycin A4.

(b) This product is dissolved in 0.5 ml of dioxan and 0.5 ml of methanol and 35 mg (0.50 mmol) of hydroxylamine hydrochloride and 1 drop of water are added. The mixture is stirred for 8 hours at room temperature. After working up with 5% aqueous NaHCO3 solution and diethyl ether, the crude product is chromatographed [20 g of silica gel/eluant: 1:3 mixture of ethyl acetate/hexane], affording 10 mg of 13β-(4'-heptylcarbonylthio)-5-oximinomilbemycin A4, for which the following spectroscopic data are obtained:

$^1$H-NMR (300 MHz; CDCl3; TMS),
3.97 ppm (d, J=10 Hz) ($C_{13}H$),
4.66 ppm (s) ($C_6H$),
7.55 ppm (s) (N—OH),
MS (FD) m/e: 713 (M+, $C_{40}H_{59}NO_8S$).

The following compounds are also obtained in accordance with Examples F1 and F2:

Example F3

13β-(2'-trifluoromethylbenzoylthio)-5-oximinomilbemycin A4

$^1$H-NMR (300 MHz; CDCl3; TMS),
4.67 ppm (s) ($C_6H$),
4.20 ppm (d, J=10 Hz) ($C_{13}H$),
7.52–7.78 ppm (m) (4 aromat. H),
MS (FD) m/e: 759 (M+, $C_{40}H_{49}NO_8SF_3$).

Example F4

13β-(3'-fluoro-2',2'-dimethylpropionylthio)-5-oximinomilbemycin A4

3.98 ppm (d, J=10 Hz) ($C_{13}H$),
4.37 ppm (d, J=47 Hz) ($CH_2F$),
4.65 ppm (s) ($C_6H$),
8.00 ppm (s) (N—OH),
MS (FD) m/e: 689 (M+, $C_{37}H_{52}NO_8SF$).

Example F5

13β-((R/S)-2'-phenylpropionylthio)-5-oximino-milbemycin A4; mixture of diastereoisomers $^1$H-NMR (300 MHz; CDCl3; TMS),
3.83 and 3.85 ppm (2q, J=6 Hz) ($C'_2$, H),
4.63 and 4.64 ppm (2s, ($C_6H$),
3.91 and 3.94 ppm (2d, J=10 Hz) ($C_{13}H$),
7.18–7.36 ppm (m) (5 aromat. H).

Example F6

13β-(2',2'-dimethylbutyrylthio)-5-oximinomilbemycin A4

$^1$H-NMR (300 MHz; CDCl3; TMS),
3.92 ppm (d, J=10 Hz) ($C_{13}H$),
4.65 ppm (s) ($C_6H$),
7.75–8,20 ppm (m) (N—OH),
MS (FD) m/e: 658 (M+, $C_{38}H_{55}NO_8S$).

Example F7

13β-(3'-chloro-2',2'-dimethylpropionylthio)-5-oximinomilbemycin A4

$^1$H-NMR (300 MHz; CDCl3; TMS),
3.59 ppm (AB-system, J=12 Hz, A-part 3,56 ppm, B-part 3,62 ppm) ($CH_2Cl$),
4.98 ppm (d, J=10 Hz) ($C_{13}H$),
4.65 ppm (s) ($C_6H$),
7,87 ppm (s) (N—OH),
MS (FD) m/e: 705 (M+, $C_{37}H_{52}ClNO_8S$).

Example F8

13β-((S)-2'-phenylpropionylthio)-5-oximinomilbemycin A4

$^1$H-NMR (300 MHz; CDCl3; TMS),
3.83 ppm (q, J=6 Hz) ($C'_2$, H),
3.93 ppm (d, J=10 Hz) ($C_{13}H$),
4.64 ppm (s) ($C_6H$),
7.20–7.36 ppm (m) (5 aromat. H),
7.81 ppm (s) (N—OH),
MS (FD) m/e: 719 (M+, $C_{41}H_{53}NO_8S$).

Example F9

13β-((R)-2'-phenylpropionylthio)-5-oximinomilbemycin A4

$^1$H-NMR (300 MHz; CDCl3; TMS),
3.85 ppm (q, J=6 Hz) ($C'_2$, H),
3.92 ppm (d, J=10 Hz) ($C_{13}H$),
4.63 ppm (s) ($C_6H$),
7.18–7.35 ppm (m) (5 aromat. H),
7.91 ppm (s) (N—OH),
MS (FD) m/e: 719 (M+, $C_{41}H_{53}NO_8S$).

Example F10

13β-(2',3'-(difluoromethylendioxi)benzoylthio)-5-oximinomilbemycin A4

$^1$NMR (300 MHz; CDCl3; TMS),
3.36 ppm (m) ($C_2H$),
4.66 ppm (s) ($C_6H$),
4.27 ppm (d, J=10 Hz) ($C_{13}H$),
7.09 ppm–7,63 ppm (m) (3 aromat. H),
7.94 ppm (s) (N—OH),
MS (FD) m/e: 771 (M+, $C_{40}H_{47}F_2NO_{10}$).

The following compounds of formula I, together with compounds of the preceding Examples, are also prepared in accordance with the procedures described above:

TABLE 1

| Typical representatives of compounds of formula I, wherein $R_1$ is hydrogen. | | |
|---|---|---|
| Comp. | $R_2$ | R |
| 1.1 | $CH_3$ | H |
| 1.2 | $C_2H_5$ | H |
| 1.3 | $isoC_3H_7$ | H |
| 1.4 | $sec-C_4H_9$ | H |
| 1.5 | $CH_3$ | $CH_3$ |
| 1.6 | $C_2H_5$ | $CH_3$ |
| 1.7 | $isoC_3H_7$ | $CH_3$ |
| 1.8 | $sec-C_4H_9$ | $CH_3$ |
| 1.9 | $CH_3$ | $C(CH_3)_3$ |
| 1.10 | $C_2H_5$ | $C(CH_3)_3$ |
| 1.11 | $isoC_3H_7$ | $C(CH_3)_3$ |
| 1.12 | $sec-C_4H_9$ | $C(CH_3)_3$ |
| 1.13 | $CH_3$ | $CH_3OCH_2$ |
| 1.14 | $C_2H_5$ | $CH_3OCH_2$ |
| 1.15 | $isoC_3H_7$ | $CH_3OCH_2$ |
| 1.16 | $sec-C_4H_9$ | $CH_3OCH_2$ |
| 1.17 | $CH_3$ | $CH_3OC(CH_3)_2$ |
| 1.18 | $C_2H_5$ | $CH_3OC(CH_3)_2$ |
| 1.19 | $isoC_3H_7$ | $CH_3OC(CH_3)_2$ |
| 1.20 | $sec-C_4H_9$ | $CH_3OC(CH_3)_2$ |
| 1.21 | $CH_3$ | $(CH_3)_2CH$ |
| 1.22 | $C_2H_5$ | $(CH_3)_2CH$ |
| 1.23 | $isoC_3H_7$ | $(CH_3)_2CH$ |

TABLE 1-continued

Typical representatives of compounds of formula I, wherein $R_1$ is hydrogen.

| Comp. | $R_2$ | R |
|---|---|---|
| 1.24 | sec-$C_4H_9$ | $(CH_3)_2CH$ |
| 1.25 | $CH_3$ | $CCl_3$ |
| 1.26 | $C_2H_5$ | $CCl_3$ |
| 1.27 | iso$C_3H_7$ | $CCl_3$ |
| 1.28 | sec-$C_4H_9$ | $CCl_3$ |
| 1.29 | $CH_3$ | $CF_3$ |
| 1.30 | $C_2H_5$ | $CF_3$ |
| 1.31 | iso$C_3H_7$ | $CF_3CHCl$ |
| 1.32 | sec-$C_4H_9$ | $CF_3$ |
| 1.33 | $CH_3$ | $C(Cl_3)CHCl$ |
| 1.34 | $C_2H_5$ | $C(Cl_3)CHCl$ |
| 1.35 | iso$C_3H_7$ | $CF_3CH_2$ |
| 1.36 | sec-$C_4H_9$ | $C(Cl_3)CHCl$ |
| 1.37 | $CH_3$ | $ClCH_2CH_2CH_2$ |
| 1.38 | $C_2H_5$ | $ClCH_2CH_2CH_2$ |
| 1.39 | iso$C_3H_7$ | $ClCH_2CH_2CH_2$ |
| 1.40 | sec-$C_4H_9$ | $ClCH_2CH_2CH_2$ |
| 1.41 | $CH_3$ | $CH_2=CH$ |
| 1.42 | $C_2H_5$ | $CH_2=CH$ |
| 1.43 | iso$C_3H_7$ | $CH_2=CH$ |
| 1.44 | sec-$C_4H_9$ | $CH_2=CH$ |
| 1.45 | $CH_3$ | $CH_2=CH-CH_2$ |
| 1.46 | $C_2H_5$ | $CH_2=CH-CH_2$ |
| 1.47 | iso$C_3H_7$ | $CH_2=CH-CH_2$ |
| 1.48 | sec-$C_4H_9$ | $CH_2=CH-CH_2$ |
| 1.49 | $CH_3$ | $CH\equiv C-CH_2$ |
| 1.50 | $C_2H_5$ | $CH\equiv C-CH_2$ |
| 1.51 | iso$C_3H_7$ | $CH\equiv C-CH_2$ |
| 1.52 | sec-$C_4H_9$ | $CH\equiv C-CH_2$ |
| 1.53 | $CH_3$ | $(CH_3)_2C=CH$ |
| 1.54 | $C_2H_5$ | $(CH_3)_2C=CH$ |
| 1.55 | iso$C_3H_7$ | $(CH_3)_2C=CH$ |
| 1.56 | sec-$C_4H_9$ | $(CH_3)_2C=CH$ |
| 1.57 | $CH_3$ | $(Cl)_2C=C(Cl)$ |
| 1.58 | $C_2H_5$ | $(Cl)_2C=C(Cl)$ |
| 1.59 | iso$C_3H_7$ | $(Cl)_2C=C(Cl)$ |
| 1.60 | sec-$C_4H_9$ | $(Cl)_2C=C(Cl)$ |
| 1.61 | $CH_3$ | $CF_3CCl_2$ |
| 1.62 | $C_2H_5$ | $CF_3CCl_2$ |
| 1.63 | iso$C_3H_7$ | $CF_3CCl_2$ |
| 1.64 | sec-$C_4H_9$ | $CF_3CCl_2$ |
| 1.65 | $CH_3$ | cyclopropyl |
| 1.66 | $C_2H_5$ | cyclopropyl |
| 1.67 | iso$C_3H_7$ | cyclopropyl |
| 1.68 | sec-$C_4H_9$ | cyclopropyl |
| 1.69 | $CH_3$ | 2,2-dimethyl-cyclopropyl |
| 1.70 | $C_2H_5$ | 2,2-dimethyl-cyclopropyl |
| 1.71 | iso$C_3H_7$ | 2,2-dimethyl-cyclopropyl |
| 1.72 | sec-$C_4H_9$ | 2,2-dimethyl-cyclopropyl |
| 1.73 | $CH_3$ | 2,2-dimethyl-3-(2,2-dichlorovinyl)cyclopropyl |
| 1.74 | $C_2H_5$ | 2,2-dimethyl-3-(2,2-dichlorovinyl)cyclopropyl |
| 1.75 | iso$C_3H_7$ | 2,2-dimethyl-3-(2,2-dichlorovinyl)cyclopropyl |
| 1.76 | sec-$C_4H_9$ | 2,2-dimethyl-3-(2,2-dichlorovinyl)cyclopropyl |
| 1.77 | $CH_3$ | cyclobutyl |
| 1.78 | $C_2H_5$ | cyclobutyl |
| 1.79 | iso$C_3H_7$ | cyclobutyl |
| 1.80 | sec-$C_4H_9$ | cyclobutyl |
| 1.81 | $CH_3$ | cyclohexyl |
| 1.82 | $C_2H_5$ | cyclohexyl |
| 1.83 | iso$C_3H_7$ | cyclohexyl |
| 1.84 | sec-$C_4H_9$ | cyclohexyl |
| 1.85 | $CH_3$ | phenyl |
| 1.86 | $C_2H_5$ | phenyl |
| 1.87 | iso$C_3H_7$ | phenyl |
| 1.88 | sec-$C_4H_9$ | phenyl |
| 1.89 | $CH_3$ | p-chlorophenyl |
| 1.90 | $C_2H_5$ | p-chlorophenyl |
| 1.91 | iso$C_3H_7$ | p-chlorophenyl |
| 1.92 | sec-$C_4H_9$ | p-chlorophenyl |
| 1.93 | $CH_3$ | p-tolyl |
| 1.94 | $C_2H_5$ | p-tolyl |
| 1.95 | iso$C_3H_7$ | p-tolyl |
| 1.96 | sec-$C_4H_9$ | p-tolyl |
| 1.97 | $CH_3$ | p-nitrophenyl |
| 1.98 | $C_2H_5$ | p-nitrophenyl |
| 1.99 | iso$C_3H_7$ | p-nitrophenyl |
| 2.00 | sec-$C_4H_9$ | p-nitrophenyl |
| 2.1 | $CH_3$ | n-hexyl |
| 2.2 | $C_2H_5$ | n-hexyl |
| 2.3 | iso$C_3H_7$ | n-hexyl |
| 2.4 | sec-$C_4H_9$ | n-hexyl |
| 2.5 | $CH_3$ | $ClCH_2C(CH_3)_2$ |
| 2.6 | $C_2H_5$ | $ClCH_2C(CH_3)_2$ |
| 2.7 | iso$C_3H_7$ | $ClCH_2C(CH_3)_2$ |
| 2.8 | sec-$C_4H_9$ | $ClCH_2C(CH_3)_2$ |
| 2.9 | $CH_3$ | 1-methylcyclopropyl |
| 2.10 | $C_2H_5$ | 1-methylcyclopropyl |
| 2.11 | iso$C_3H_7$ | 1-methylcyclopropyl |
| 2.12 | sec-$C_4H_9$ | 1-methylcyclopropyl |
| 2.13 | $CH_3$ | adamantyl |
| 2.14 | $C_2H_5$ | adamantyl |
| 2.15 | iso$C_3H_7$ | adamantyl |
| 2.16 | sec-$C_4H_9$ | adamantyl |
| 2.17 | $C_2H_5$ | p-fluorophenoxymethyl |
| 2.18 | $C_2H_5$ | $ClC(CH_3)_2$ |
| 2.19 | $C_2H_5$ | $CH_3CCl_2$ |
| 2.20 | $C_2H_5$ | $CH_3CH_2C(CH_3)_2$ |
| 2.21 | $C_2H_5$ | $C(CH_3)_3CH_2$ |
| 2.22 | $C_2H_5$ | $C(CH_3)_3C(CH_3)_2$ |
| 2.23 | $C_2H_5$ | $ClCH_2$ |
| 2.24 | $C_2H_5$ | $CF_3CH_2$ |
| 2.25 | $C_2H_5$ | 1-methylcyclobutyl |
| 2.26 | $C_2H_5$ | 1-methylcyclopentyl |
| 2.27 | $C_2H_5$ | $FCH_2C(CH_3)_2$ |
| 2.28 | $C_2H_5$ | $CH_2=C(CH_3)$ |
| 2.29 | $C_2H_5$ | $ClCH_2CH_2$ |
| 2.30 | $C_2H_5$ | p-(tert-$C_4H_9$)phenyl |
| 2.31 | $C_2H_5$ | $CH_3CH_2CH_2$ |
| 2.32 | $C_2H_5$ | $CH_3CH_2$ |
| 2.33 | $C_2H_5$ | $CF_3C_6H_4$ |
| 2.34 | $C_2H_5$ | $C_6H_5(CH_3)CH$ |
| 2.35 | $C_2H_5$ | $(S)-C_6H_5(CH_3)CH$ |
| 2.36 | $C_2H_5$ | $(R)-C_6H_5(CH_3)CH$ |
| 2.37 | $C_2H_5$ | $C_6H_5(CH_3)_2C$ |
| 2.38 | $C_2H_5$ | $(CH_3CH_2CH_2)_2CH$ |
| 2.41 | $C_2H_5$ | $CH_3S(CH_3)_2C$ |
| 2.51 | $C_2H_5$ | o-(trifluoromethyl)phenyl |

The contents of this Table is illustrative and constitutes no limitation. Further typical representatives are compounds of formula I in which $R_2$ and R are as defined in the Table and $R_1$ is an alkyl, cycloalkyl or acyl group.

Formulation Examples for active ingredients of formula I (throughout, percentages are by weight)

| Wettable powders | (a) | (b) | (c) |
|---|---|---|---|
| compound of Table 1 | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| Emulsifiable concentrate | |
|---|---|
| compound of Table 1 | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| Dusts | (a) | (b) |
|---|---|---|
| compound of Table 1 | 5% | 8% |
| talcum | 95% | — |
| kaolin | — | 92% |

Ready for use dusts are obtained by mixing the active ingredient with the carrier, and grinding the mixture in a suitable mill.

| Extruder granulate | |
|---|---|
| compound of Table 1 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| Tablets or pellets | | |
|---|---|---|
| I | compound of Table 1 | 33.00% |
| | methyl cellulose | 0.80% |
| | highly dispersed silicic acid | 0.80% |
| | maize starch | 8.40% |

The methyl cellulose is stirred in water and allowed to swell. Then the silicic acid is stirred in to give a homogeneous suspension. The compound of formula I and the maize starch are mixed and the aqueous suspension is added to the mix, which is kneaded to a paste. This paste is granulated through a 12M sieve and the granulate is dried.

| | | |
|---|---|---|
| II | crystalline lactose | 22.50% |
| | maize starch | 17.00% |
| | microcrystalline cellulose | 16.5% |
| | magnesium stearate | 1.00% |

All 4 adjuvants are thoroughly mixed. Phases I and II are mixed and compressed to tablets or pellets.

If the compounds of formula I, or compositions containing them, are used for controlling endoparasitic nematodes, cestodes and trematodes in domestic animals and productive livestock, for example cattle, sheep, goats, cats and dogs, they can be administered to the animals in both single and repeated doses. Depending on the species of animal, the individual doses are preferably administered in amounts ranging from 0.1 to 10 mg/kg of body weight. A better action is often achieved by protracted administration, or lower total doses will also suffice. The compounds, or compositions containing them, can also be added to feeds and drinks. The ready-prepared feeds contain the active ingredients preferably in a concentration of 0.005 to 0.1 percent by weight. The compositions can be administered to the animals perorally in the form of solutions, emulsions, suspensions, powders, tablets, pellets, boluses or capsules.

If the physical and toxicological properties of solutions or emulsions permit it, the compounds of formula I, or compositions containing them, can also be injected into animals for example subcutaneously, administered intraruminally or applied to the bodies of the animals by the pour-on method. Administration by means of salt licks or molasses blocks is also possible.

Biological Examples

B1: Action against $L_1$ larvae of Lucilia sericata 1 ml of an aqueous suspension of test compound is mixed with 3 ml of a special larval culture medium at about 50° C. such that a homogeneous composition containing 250 ppm or 125 ppm is obtained. About 30 Lucilia sericata larvae ($L_1$) are put into each test tube containing active ingredient. A mortality count is made after 4 days. Compounds of formula I are 100% effective at 250 ppm.

B2: Acaricidal action against Boophilus microplus (Biarra strain)

Adhesive tape is applied horizontally across a PVC plate so that 10 fully replete female Boophilus microplus ticks (Biarra strain) can be affixed thereto with their backs, side by side, in a row. Each tick is injected from an injection needle with 1 μl of a liquid which contains a 1:1 mixture of polyethylene glycol and acetone, in which mixture a specific amount of test compound of 1, 0.5, 0.1 or 0.01 μg per tick is dissolved. Control ticks are injected with liquid containing no test compound. After this treatment, the ticks are detached from the support and kept in an insectarium under normal conditions at about 28° C. and 80% relative humidity until oviposition has taken place and the larvae have hatched from the eggs of the control ticks. The activity of the test compound is determined with the $IR_{90}$, i.e. the effective dose is determined at which 9 out of 10 female ticks (90%) even after 30 days lay eggs from which larvae are unable to hatch.

Compounds of formula I achieve an $IR_{10}$ at 0.5 μg. Compound 1.10 (Table 1) is also effective against the nymphal stages of Boophilus and other ticks.

B3: Trial with sheep infected with nematodes (Haemonchus contortus and Trichostrongylus colubriformis)

The test compound is administered in the form of a suspension with a stomach probe or by intraruminal injection to sheep which have been artificially infected with Haemonchus contortus and Trichostrongylus colubriformis. One to three animals are used for each dose. Each sheep is treated only once with a single dose of 0.5 mg of body weight. Evaluation is made by comparing the number of worm eggs excreted in the faeces of the sheep before and after treatment.

Untreated sheep infected simultaneously and in the same manner are used as controls. In comparison with untreated and infected control groups, there is no nematode infestation (=complete reduction of the number of worm eggs in the faeces) in sheep which have been treated with one of the compounds of formula I.

B4: Larvicidal action against Aëdes aegypti

A 0.1% solution of the test compound in acetone is pipetted onto the surface of 150 ml of water in beakers in amounts sufficient to give concentrations of 10 ppm, 3.3 ppm and 1.6 ppm. After the acetone has evaporated, 30 to 40 three-day-old larvae of *Aëdes aegypti* are put into each beaker. Mortality counts are made after 1, 2 and 5 days.

In this test, compounds of formula I achieve complete kill of all larvae at a concentration of 1.6 ppm even after 1 day.

B.5 Milbicidal action against *Dermanyssus gallinae*

2 to 3 ml of a test solution (100, 10, 1 and 0.1 ppm of test compound) are put into a glass container which is open at the top and about 200 mites in different stages of development are put into this container. The container is then sealed with cotton wool and shaken uniformly for 10 minutes until the mites are completely wetted. The container is then inverted until excess test solution has been absorbed by the cotton wool. The container is again inverted and the treated mites are kept under observation for 3 days under laboratory conditions to evaluate the effectiveness of the test compounds. Mortality is the criterion for effectiveness.

Compounds of the Examples effect 100% kill at a concentration of 100 ppm.

What is claimed is:

1. A compound of formula I

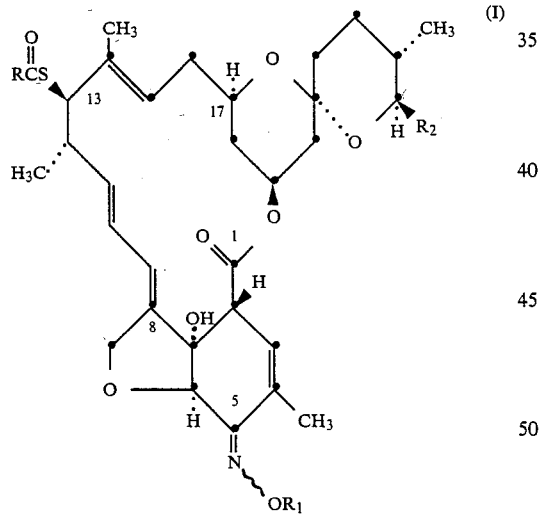

wherein
$R_1$ is hydrogen,
$R_2$ is methyl, ethyl, isopropyl or sec-butyl, or is the

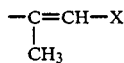

group, wherein X is methyl, ethyl or isopropyl, and R is hydrogen; or is straight chain or branched $C_1$-$C_{18}$alkyl which is unsubstituted or substituted by 1 to 7 halogen atoms, 1 to 6 $C_1$-$C_6$alkylthio, 1 to 6 $C_1$-$C_6$alkoxy or an unsubstituted or halogenated phenyl or phenoxy group; or is $C_2$-$C_6$alkenyl which is unsubstituted or substituted by 1 to 7 halogen atoms, 1 to 6 $C_1$-$C_6$alkylthio or 1 to 6 $C_1$-$C_6$alkoxy; or is $C_2$-$C_6$alkynyl which is unsubstituted or substituted by 1 to 7 halogen atoms, 1 to 6 $C_1$-$C_6$alkylthio or 1 to 6 $C_1$-$C_6$alkoxy; or is $C_3$-$C_6$cycloalkyl which is unsubstituted or substituted by 1 to 7 halogen atoms, 1 to 6 $C_1$-$C_6$alkylthio, 1 to 6 $C_1$-$C_6$alkoxy or by $C_1$-$C_4$alkyl groups and, if said cycloalkyl is cyclopropyl, it may also be substituted by 2,2-dichlorovinyl; or is a phenyl or benzyl group each unsubstituted or substituted by 1 to 3 substituents selected from the group consisting of halogen atoms, $C_1$-$C_6$alkyl, $C_1$-$C_6$alkoxy, $C_1$-$C_4$alkylthio, $CHCl_2$, $CHF_2$, $CH_2Cl$, $CCl_3$, $CF_3$, $CH_2F$, $CH_2CH_2Cl$, $CHBr_2$ and nitro; or is difluoromethylenedioxyphenyl, wherein the oxygen atoms are located at directly adjacent carbon atoms of the phenyl ring.

2. A compound of formula Ia according to claim 1

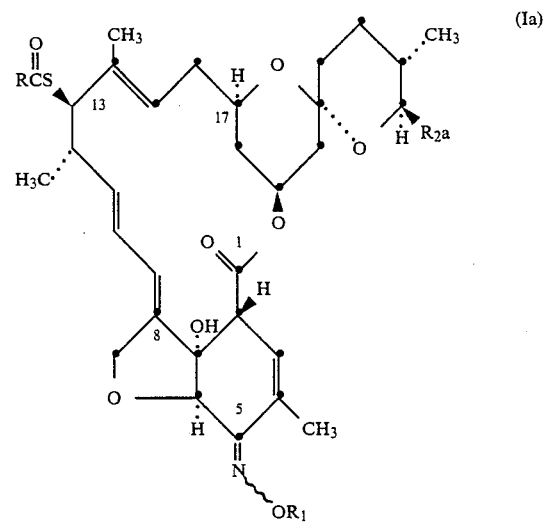

wherein
$R_1$ is hydrogen and
$R_{2a}$ is methyl, ethyl, isopropyl or sec-butyl.

3. A compound of formula I according to claim 1, wherein the alkyl, cycloalkyl, alkenyl and alkynyl groups R are each substituted by 1 to 7 halogen atoms or 1 to 6 $C_1$-$C_6$alkoxy groups, and the phenyl group is substituted by 1 to 3 substituents selected from the group consisting of halogen atoms, $C_1$-$C_6$alkyl, $C_1$-$C_6$alkoxy, $C_1$-$C_4$alkylthio and nitro, $R_2$ is methyl, ethyl, isopropyl or sec-butyl and $R_1$ is as defined for formula I in claim 1.

4. A compound of formula I according to claim 1, wherein $R_1$ is hydrogen, $R_2$ is methyl, ethyl, isopropyl or sec-butyl and R is hydrogen, or $C_1$-$C_6$alkyl, $C_2$-$C_4$alkenyl, $C_2$-$C_4$alkynyl or $C_3$-$C_6$cycloalkyl, each unsubstituted or substituted by 1 to 4 halogen atoms or 1 to 4 $C_1$-$C_4$alkylthio or $C_1$-$C_4$alkoxy groups; or is phenyl which is unsubstituted or substituted by 1 to 3 substituents selected from the group consisting of halogen, $C_1$-$C_4$alkyl, $C_1$-$C_4$alkoxy, $C_1$-$C_4$alkylthio and nitro.

5. A compound of formula I according to claim 1, wherein $R_1$ is hydrogen, $R_2$ is methyl, ethyl, isopropyl or sec-butyl and R is hydrogen, or $C_1$-$C_4$alkyl, $C_2$-$C_3$alkenyl, $C_2$-$C_3$alkynyl or $C_3$-$C_6$cycloalkyl, each unsubstituted or substituted by 1 to 4 chlorine or fluorine atoms or 1 to 4 methylthio or methoxy groups; or is phenyl or benzyl, each unsubstituted or substituted by chlorine, fluorine, $C_1$-$C_2$alkyl, $C_1$-$C_2$alkoxy, $C_1$-$C_2$alkylthio or nitro.

6. A compound of formula I according to claim 1, wherein $R_1$ is hydrogen, $R_2$ is ethyl or methyl and R is hydrogen; $C_1$-$C_8$alkyl which is unsubstituted or monosubstituted by $C_1$-$C_4$alkoxy or by mono- to trihalogenated phenoxy or is substituted by 1 to 5 halogen atoms; or is a mono cyclic aliphatic group which contains a total of 3 to 6 carbon atoms in the ring or ring system and which is unsubstituted or substituted by one to 4 $C_1$-$C_4$alkyl groups; or is mono- to trihalogenated $C_2$-$C_4$alkenyl; $C_3$-$C_4$alkynyl; or phenyl or benzyl each substituted by 1 to 3 substituents selected from the group consisting of halogen, $C_1$-$C_4$alkyl and nitro.

7. A compound of formula I according to claim 1, wherein $R_1$ is hydrogen, $R_2$ is ethyl or methyl and R is hydrogen; $C_1$-$C_8$alkyl which is unsubstituted or substituted by 1 to 3 substituents selected from the group consisting of chlorine and fluorine; or is fluorophenoxymethyl; $C_3$-$C_4$cycloalkyl which is unsubstituted or substituted by a methyl group; or is trichlorovinyl, phenyl or monochlorophenyl.

8. A compound according to claim 1, selected from the group consisting of:
13$\beta$-formylthio-5-oximino-milbemycin D,
13$\beta$-acetylthio-5-oximino-milbemycin D,
13$\beta$-pivaloylthio-5-oximino-milbemycin D,
13$\beta$-formylthio-5-oximino-milbemycin $A_3$,
13$\beta$-acetylthio-5-oximino-milbemycin $A_3$,
13$\beta$-pivaloylthio-5-oximino-milbemycin $A_3$,
13$\beta$-formylthio-5-oximino-milbemycin $A_4$,
13$\beta$-acetylthio-5-oximino-milbemycin $A_4$,
13$\beta$-pivaloylthio-5-oximino-milbemycin $A_4$,
13$\beta$-(2'-methoxy-2'-methylpropionylthio)-5-oximino-milbemycin D,
13$\beta$-(2'-methoxy-2'-methylpropionylthio)-5-oximino-milbemycin $A_4$,
13$\beta$-trichloroacetylthio-5-oximino-milbemycin $A_4$,
13$\beta$-(4'-chloro-butanoylthio)-5-oximino-milbemycin $A_4$,
13$\beta$-trichloroacryloylthio-5-oximino-milbemycin $A_4$,
13$\beta$-cyclopropanecarbonylthio-5-oximino-milbemycin $A_4$,
13$\beta$-cyclobutanecarbonylthio-5-oximino-milbemycin $A_4$,
13$\beta$-heptanoylthio-5-oximino-milbemycin $A_4$,
13$\beta$-(3'-chloro-2',2'-dimethylpropionylthio)-5-oximino-milbemycin $A_4$,
13$\beta$-(3'-chloro-2',2'-dimethylpropionylthio)-5-oximino-milbemycin $A_3$,
13$\beta$-(1'-methyl-cyclopropanecarbonylthio)-5-oximino-milbemycin $A_4$,
13$\beta$-(1'-methyl-cyclopropanecarbonylthio)-5-oximino-milbemycin $A_3$,
13$\beta$-(p-fluorophenoxyacetylthio)-5-oximino-milbemycin $A_4$,
13$\beta$-(2'-chloro-2'-methylpropionylthio)-5-oximino-milbemycin $A_4$,
13$\beta$-(2',2'-dichloropropionylthio)-5-oximino-milbemycin $A_4$,
13$\beta$-(2',2'-dimethylbutanoylthio)-5-oximino-milbemycin $A_4$,
13$\beta$-(3',3'-dimethylbutanoylthio)-5-oximino-milbemycin $A_4$,
13$\beta$-(2',2', 3',3'-tetramethylbutanoylthio)-5-oximino-milbemycin $A_4$,
13$\beta$-(p-chlorobenzoylthio)-5-oximino-milbemycin $A_4$,
13$\beta$-(3',3',3'-trifluoropropionylthio)-5-oximino-milbemycin $A_4$,
13$\beta$-chloroacetylthio-5-oximino-milbemycin $A_4$,
13$\beta$-(2'-chloro-3',3', 3'-trifluorpropionylthio)-5-oximino-milbemycin $A_4$,
13$\beta$-(3',3', 3'-trifluoropropionylthio)-5-oximino-milbemycin $A_4$,
13$\beta$-(4'-heptylcarbonylthio)-5-oximino-milbemycin $A_4$,
13$\beta$-(4'-heptylcarbonylthio)-5-oximino-milbemycin $A_3$,
13$\beta$-(2'-trifluoromethylbenzoylthio)-5-oximino-milbemycin $A_4$,
13$\beta$-(2'-trifluoromethylbenzoylthio)-5-oximino-milbemycin $A_3$,
13$\beta$-((R/S)-2'-phenylpropionylthio)-5-oximino-milbemycin $A_4$,
13$\beta$-((R/S)-2'-phenylpropionylthio)-5-oximino-milbemycin $A_3$,
13$\beta$-(2,2'-dimethylbutyrylthio)-5-oximino-milbemycin $A_4$,
13$\beta$-(2,2'-dimethylbutyrylthio)-5-oximino-milbemycin $A_3$,
13$\beta$-(3'-fluoro-2',2'-dimethylpropionylthio)-5-oximino-milbemycin $A_4$,
13$\beta$-(3'-fluoro-2',2'-dimethylpropionylthio)-5-oximino-milbemycin $A_3$,
13$\beta$-(methoxyacetylthio)-5-oximino-milbemycin $A_4$,
13$\beta$-(methoxyacetylthio)-5-oximino-milbemycin $A_3$,
13$\beta$-(2'3'-(difluoromethylendioxy)benzoylthio-5-oximino-milbemycin $A_4$,
13$\beta$-(2'3'-(difluoromethylendioxy)benzoylthio-5-oximino-milbemycin $A_3$.

9. A method of controlling pests, which method comprises applying or administering to the host animals or applying to the host plants or to other loci of said pests a pesticidally effective amount of at least one compound of formula I according to claim 1.

10. A method of controlling pests, which method comprises applying or administering to the host animals or applying to the host plants or to other loci of said pests a pesticidally effective amount of at least one compound of formula Ia according to claim 2.

11. A method according to claim 9, wherein the pests to be controlled are endoparasites or ectoparasites that attack animals.

12. A method according to claim 10, wherein the pests to be controlled are endoparasites or ectoparasites that attack animals.

13. A pesticidal composition for controlling ecto- and endoparasites and insects, which contains an inert carrier and at least one compound of formula I

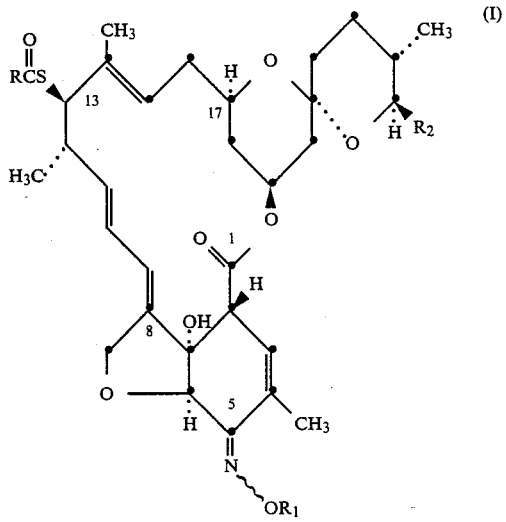

wherein
R₁ is hydrogen,
R₂ is methyl, ethyl, isopropyl or sec-butyl, or is the

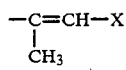

group, wherein X is methyl, ethyl or isopropyl, and R is hydrogen; or is straight chain or branched $C_1$–$C_{18}$alkyl which is unsubstituted or substituted by 1 to 7 halogen atoms, 1 to 6 $C_1$–$C_6$alkylthio, 1 to 6 $C_1$–$C_6$alkoxy or an unsubstituted or one to three times halogenated phenyl or phenoxy group; or is $C_2$–$C_6$alkenyl which is unsubsituted or substituted by 1 to 7 halogen atoms, 1 to 6 $C_1$–$C_6$alkylthio or 1 to 6 $C_1$–$C_6$alkoxy; or is $C_2$–$C_6$alkynyl which is unsubstituted or substituted by 1 to 7 halogen atoms, 1 to 6 $C_1$–$C_6$alkylthio or 1 to 6 $C_1$–$C_6$alkoxy; or is $C_3$–$C_6$cycloalkyl which is unsubstituted or substituted by 1 to 7 halogen atoms, 1 to 6 $C_1$–$C_6$alkylthio, 1 to 6 $C_1$–$C_6$alkoxy or by $C_1$–$C_4$alkyl groups and, if said cycloalkyl is cyclopropyl, it may also be substituted by 2,2-dichlorovinyl; or is a phenyl or benzyl group each unsubstituted or substituted by 1 to 3 substituents selected from the group consisting of halogen atoms, $C_1$–$C_6$alkyl, $C_1$–$C_6$alkoxy, $C_1$–$C_4$alkylthio, $CHCl_2$, $CHF_2$, $CH_2Cl$, $CCl_3$, $CF_3$, $CH_2F$, $CH_2CH_2Cl$, $CHBr_2$ and nitro; or is difluoromethylenedioxyphenyl, wherein the oxygen atoms are located at directly adjacent carbon atoms of the phenyl ring.

14. A composition according to claim 13, which contains an inert carrier and at least one compound of formula Ia

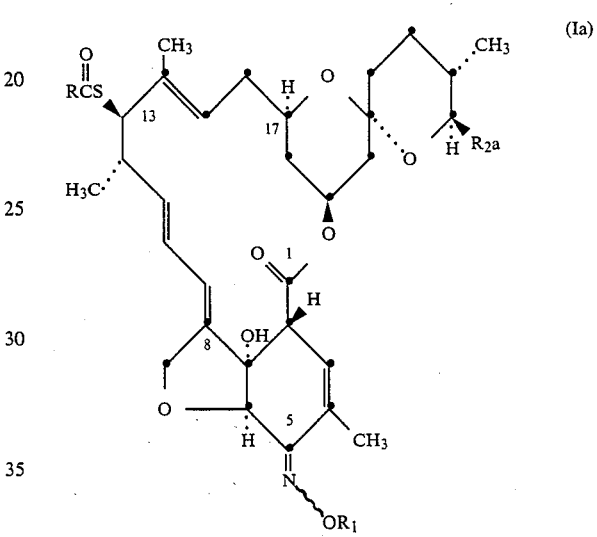

wherein
R₁ is hydrogen and
R₂ₐ is methyl, ethyl, isopropyl or sec-butyl.

* * * * *